US006354147B1

(12) United States Patent
Gysling et al.

(10) Patent No.: US 6,354,147 B1
(45) Date of Patent: Mar. 12, 2002

(54) FLUID PARAMETER MEASUREMENT IN PIPES USING ACOUSTIC PRESSURES

(75) Inventors: Daniel L. Gysling; Alan D. Kersey, both of Glastonbury, CT (US); James D. Paduano, Arlington, MA (US)

(73) Assignee: CiDRA Corporation, Wallingford, CT (US)

( * ) Notice: Subject to any disclaimer, the term of this patent is extended or adjusted under 35 U.S.C. 154(b) by 0 days.

(21) Appl. No.: 09/344,094

(22) Filed: Jun. 25, 1999

Related U.S. Application Data

(63) Continuation-in-part of application No. 09/105,534, filed on Jun. 26, 1998, now abandoned.

(51) Int. Cl.[7] .............................................. G01N 29/00

(52) U.S. Cl. .................... 73/61.79; 73/61.47; 73/61.49; 73/579; 73/643; 73/653; 73/656; 73/657

(58) Field of Search ............................ 73/61.79, 61.41, 73/61.47, 61.49, 597, 643, 655, 656, 657

(56) References Cited

U.S. PATENT DOCUMENTS

| 3,851,521 A | * 12/1974 | Ottenstein ................. 73/40.5 R |
| 4,080,837 A | 3/1978 | Alexander et al. |
| 4,445,389 A | 5/1984 | Potzick et al. ............ 73/861.27 |
| 4,520,320 A | 5/1985 | Potzick et al. |
| 4,896,540 A | 1/1990 | Shakkottai et al. ....... 73/861.02 |
| 4,932,262 A | 6/1990 | Wlodarczyk ............ 250/227.23 |
| 5,040,415 A | 8/1991 | Barkhoudarian .......... 73/861.03 |
| 5,083,452 A | 1/1992 | Hope |
| 5,218,197 A | 6/1993 | Carroll |
| 5,363,342 A | 11/1994 | Layton et al. |
| 5,398,542 A | 3/1995 | Vasbinder ................. 73/40.5 A |
| 5,591,922 A | 1/1997 | Segeral et al. |
| 5,741,980 A | 4/1998 | Hill et al. |
| 5,845,033 A | 12/1998 | Berthold et al. ............... 385/12 |

FOREIGN PATENT DOCUMENTS

WO 14382 7/1993

OTHER PUBLICATIONS

Multiplexed Fiber Bragg Grating Strain–Sensor System With a Fiber Fabry–Perot Wavelength Filter, A. D. Kersey, T. A. Berkoff, and W. W. Morey, Aug. 15, 1993, vol. 18, No. 16–Optics Letters.

"Noise and Vibration Control Engineering Principles and Applications", Leo L. Beranek and Istvan L. Ver, A Wiley Interscience Publication, pp. 537–541, Aug. 1992.

* cited by examiner

*Primary Examiner*—Daniel S. Larkin

(57) ABSTRACT

At least one parameter of at least one fluid in a pipe 12 is measured using a spatial array of acoustic pressure sensors 14,16,18 placed at predetermined axial locations x1,x2,x3 along the pipe 12. The pressure sensors 14,16,18 provide acoustic pressure signals $P_1(t)$, $P_2(t)$, $P_3(t)$ on lines 20,22,24 which are provided to signal processing logic 60 which determines the speed of sound $a_{mix}$ of the fluid (or mixture) in the pipe 12 using acoustic spatial array signal processing techniques with the direction of propagation of the acoustic signals along the longitudinal axis of the pipe 12. Numerous spatial array processing techniques may be employed to determined the speed of sound $a_{mix}$. The speed of sound $a_{mix}$ is provided to logic 48 which calculates the percent composition of the mixture, e.g., water fraction, or any other parameter of the mixture or fluid which is related to the sound speed $a_{mix}$. The logic 60 may also determine the Mach number Mx of the fluid. The acoustic pressure signals $P_1(t)$, $P_2(t)$, $P_3(t)$ measured are lower frequency (and longer wavelength) signals than those used for ultrasonic flow meters, and thus is more tolerant to inhomogeneities in the flow. No external source is required and thus may operate using passive listening. The invention will work with arbitrary sensor spacing and with as few as two sensors if certain information is known about the acoustic properties of the system.

86 Claims, 19 Drawing Sheets

FLUID PARAMETER MEASUREMENT IN PIPES USING ACOUSTIC PRESSURES

CROSS REFERENCES TO RELATED APPLICATIONS

This application is an continuation-in-part of commonly owned U.S. Patent application, Ser. No., 09/105,534, entitled "Fluid Parameter Measurement in Pipes Using Acoustic Pressures", filed Jun. 26, 1998, now abandoned and contains subject matter related to that disclosed in commonly owned U.S. Patent application: Ser. No. 09/344, 070, entitled "Measurement of Propagating Acoustic Waves in Compliant Pipes", filed Jun. 25, 1999, Ser. No. 09/344, 069, entitled "Displacement Based Pressure Sensor Measuring Unsteady Pressure in a Pipe", filed Jun. 25, 1999 and Ser. No. 09/344,093, entitled "Non-Intrusive Fiber Optic Pressure Sensor for Measuring Unsteady Pressures within a Pipe", filed Jun. 25, 1999, all of which are incorporated herein by reference.

TECHNICAL FIELD

This invention relates to fluid parameter measurement in pipes and more particularly to measuring speed of sound and parameters related thereto of fluids in pipes using acoustic pressures.

BACKGROUND ART

It is known that the speed of sound $a_{mix}$ of fluids in pipes may be used to determine various parameters of the fluid, such as is described in U.S. Pat. No. 4,080,837, entitled "Sonic Measurement of Flow Rate and Water Content of Oil-Water Streams", to Alexander et al., U.S. Pat. No. 5,115,670, entitled "Measurement of Fluid Properties of Two-Phase Fluids Using an Ultrasonic Meter", to Shen, and U.S. Pat. No. 4,114,439, entitled "Apparatus for Ultrasonically Measuring Physical Parameters of Flowing Media", to Fick. Such techniques have a pair of acoustic transmitters/receivers (transceivers) which generate a sound signal and measure the time it takes for the sound signal to travel between the transceivers. This is also known as a "sing-around" or "transit time" method. However, such techniques require precise control of the acoustic source and are costly and/or complex to implement in electronics.

Also, these techniques use ultrasonic acoustic signals as the sound signal measured, which are high frequency, short wavelength signals (i.e., wavelengths that are short compared to the diameter of the pipe). Typical ultrasonic devices operate near 200k Hz, which corresponds to a wavelength of about 0.3 inches in water. In general, to allow for signal propagation through the fluid in an unimpeded and thus interpretable manner, the fluid should be homogeneous down to length scales of several times smaller than the acoustic signal wavelength. Thus, the criteria for homogeneity of the fluid becomes increasingly more strict with shorter wavelength signals. Consequently, inhomogeneities in the fluid, such as bubbles, gas, dirt, sand, slugs, stratification, globules of liquid, and the like, will reflect or scatter the transmitted ultrasonic signal. Such reflection and scattering inhibit the ability of the instrument to determine the propagation velocity. For this reason, the application of ultrasonic flowmeters have been limited primarily to well mixed flows.

SUMMARY OF THE INVENTION

Objects of the present invention include provision of a system for measuring the speed of sound of fluids in pipes.

According to the present invention, an apparatus for measuring at least one parameter of a mixture of at least one fluid in a pipe, comprising a spatial array of at least two pressure sensors, disposed at different axial locations along the pipe, and each measuring an acoustic pressure within the pipe at a corresponding axial location, each of said sensors providing an acoustic pressure signal indicative of the acoustic pressure within the pipe at said axial location of a corresponding one of said sensors; and a signal processor, responsive to said pressure signals, which provides a signal indicative of a speed of sound of the mixture in the pipe.

According further to the present invention, the signal processor comprises logic which calculates a speed at which sound propagates along the spatial array.

According further to the present invention, the signal processor comprises logic which calculates a frequency domain representation of (or frequency based signal for) each of the acoustic pressures signals. According still further to the present invention, the signal processor comprises logic which calculates a ratio of two of the frequency signals. In still further accord to the present invention, the sensors comprise at least three sensors.

According still further to the present invention, the pressure sensors are fiber optic Bragg grating-based pressure sensors. Still further accord to the present invention, at least one of the pressure sensors measures an circumferential-averaged pressure at a given axial location of the sensor. Further according to the present invention, at least one of the pressure sensors measures pressure at more than one point around a circumference of the pipe at a given axial location of the sensor.

The present invention provides a significant improvement over the prior art by providing a measurement of the speed of sound $a_{mix}$ of a mixture of one or more fluids within a pipe (where a fluid is defined as a liquid or a gas) by using an axial array of acoustic (or ac, dynamic, unsteady, or time varying) pressure measurements along the pipe. An explicit acoustic noise source is not required, as the background acoustic noises within the pipe (or fluid therein) will likely provide sufficient excitation to enable characterization of the speed of sound of the mixture by merely passive acoustic listening.

The invention works with acoustic signals having lower frequencies (and thus longer wavelengths) than those used for ultrasonic meters, such as below about 20k Hz (depending on pipe diameter). As such, the invention is more tolerant to the introduction of gas, sand, slugs, or other inhomogeneities in the flow.

The invention will work with arbitrary sensor spacing and arbitrary flow Mach numbers Mx; however, if the sensors are equally spaced and the axial velocity of the flow is small and therefore negligible compared to the speed of sound in the mixture (i.e., Mach number of the mixture Mx is small compared to one), the speed of sound $a_{mix}$ may be determined as an explicit function of the frequency domain representation (frequency based signal) for the acoustic pressure signals at a given evaluation frequency ω.

Since the speed of sound is an intrinsic property of mixtures, the present invention can be used to measure any parameter (or characteristic) of any mixture of one or more fluids in a pipe in which such parameter is related to the speed of sound of the mixture $a_{mix}$, e.g., fluid fraction, temperature, salinity, sand particles, slugs, pipe properties, etc. or any other parameter of the mixture that is related to the speed of sound of the mixture. For example, the present invention may be used to measure fluid volume fractions (or composition or cut or content) of a mixture of any number of fluids in which the speed of sound of the mixture $a_{mix}$ is related to (or is substantially determined by), the volume fractions of two constituents of the mixture, e.g., oil/water, oil/gas, water/gas. Also, the present invention can be used to measure the speed of sound of any mixture and can then be used in combination with other known quantities to derive phase content of mixtures with multiple (more than two) constituents.

The present invention allows the speed of sound to be determined in a pipe independent of pipe orientation, i.e., vertical, horizontal, or any orientation therebetween. Also, the invention does not require any disruption to the flow within the pipe (e.g., an orifice or venturi). Further, the invention uses ac (or unsteady or dynamic) pressure measurements as opposed to static (dc) pressure measurements and is therefore less sensitive to static shifts (or errors) in sensing. Furthermore, if harsh environment fiber optic pressure sensors are used to obtain the pressure measurements, such sensors eliminate the need for any electronic components down-hole, thereby improving reliability of the measurement.

Also, a strain gauge (optical, electrical, etc.) that measures hoop strain on the pipe may be used to measure the ac pressure. Fiber optic wrapped sensors may be used as optical strain gauges to provide circumferentially-averaged pressure. Thus, the present invention provides non-intrusive measurements of the speed of sound (and other corresponding parameters), which enables real time monitoring and optimization for oil and gas exploration and production, or for other applications.

The foregoing and other objects, features and advantages of the present invention will become more apparent in light of the following detailed description of exemplary embodiments thereof.

BEST MODE FOR CARRYING OUT THE INVENTION

Figure 1:
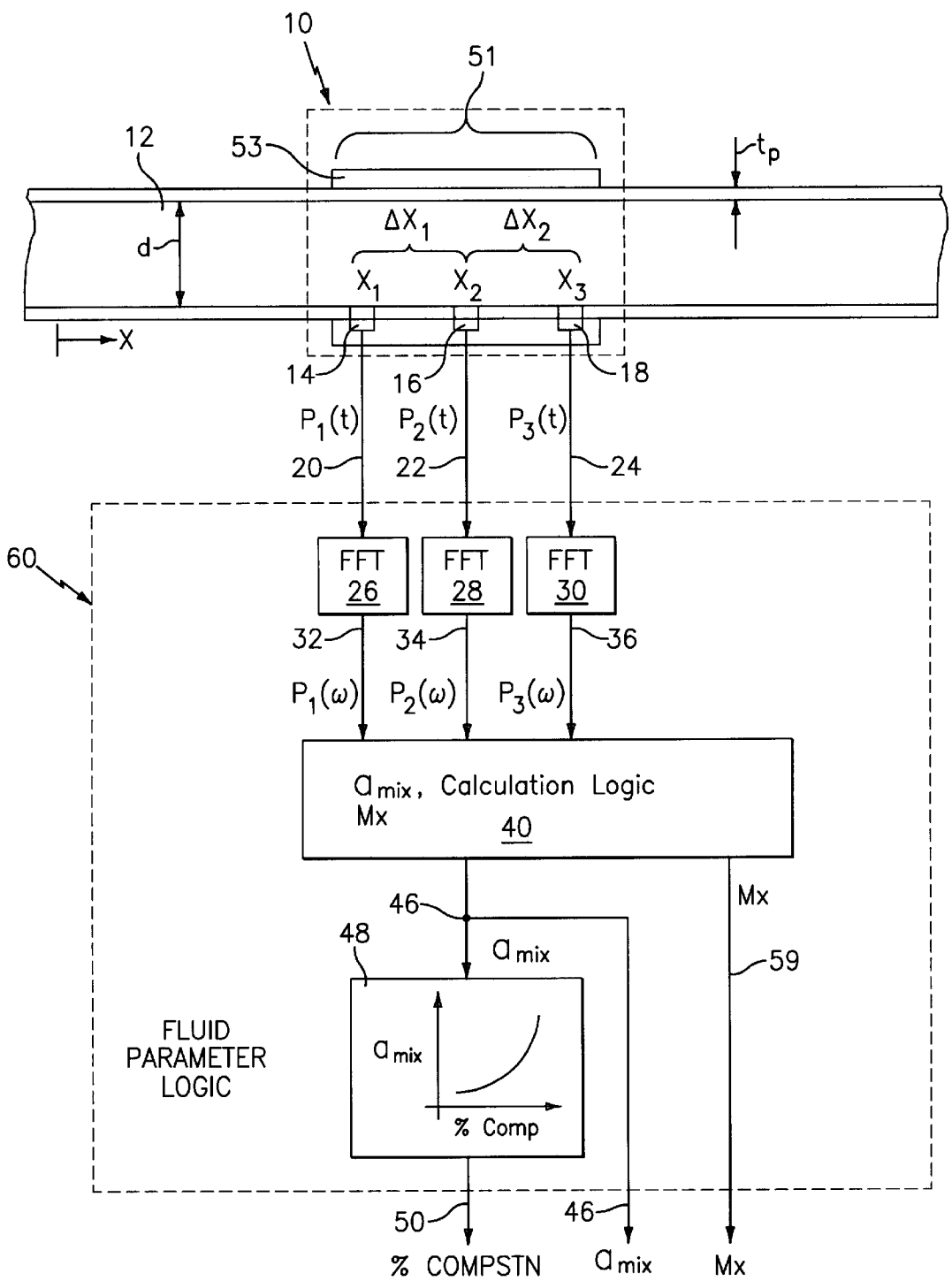
FIG. 1 is a schematic block diagram of a fluid parameter measurement system, in accordance with the present invention.

Referring to FIG. 1, a pipe (or conduit) 12 has three acoustic pressure sensors 14,16,18, located at three locations $x_1,x_2,x_3$ along the pipe 12. The pressure may be measured through holes in the pipe 12 ported to external pressure sensors or by other techniques discussed hereinafter. The pressure sensors 14,16,18 provide pressure time-varying signals $P_1(t),P_2(t),P_3(t)$ on lines 20,22,24, to known Fast Fourier Transform (FFT) logics 26,28,30, respectively. The FFT logics 26,28,30 calculate the Fourier transform of the time-based input signals $P_1(t),P_2(t),P_3(t)$ and provide complex frequency domain (or frequency based) signals $P_1(\omega)$, $P_2(\omega),P_3(\omega)$ on lines 32,34,36 indicative of the frequency content of the input signals. Instead of FFT's, any other technique for obtaining the frequency domain characteristics of the signals $P_1(t),P_2(t),P_3(t)$, may be used. For example, the cross-spectral density and the power spectral density may be used to form a frequency domain transfer functions (or frequency response or ratios) discussed hereinafter.

Also, some or all of the functions within the logic 60 may be implemented in software (using a microprocessor or computer) and/or firmware, or may be implemented using analog and/or digital hardware, having sufficient memory, interfaces, and capacity to perform the functions described herein.

The frequency signals $P_1(\omega),P_2(\omega),P_3(\omega)$ are fed to $a_{mix}$-Mx Calculation Logic 40 which provides a signal on a line 46 indicative of the speed of sound of the mixture $a_{mix}$ (discussed more hereinafter). The $a_{mix}$ signal is provided to map (or equation) logic 48, which converts $a_{mix}$ to a percent composition of the fluid and provides a % Comp signal on a line 50 indicative thereof (as discussed hereinafter). Also, if the Mach number Mx is not negligible and is desired to be known, the calculation logic 40 may also provide a signal Mx on a line 59 indicative of the Mach number Mx (as discussed hereinafter).

More specifically, for planar one-dimensional acoustic waves in a homogenous mixture, it is known that the acoustic pressure field P(x,t) at a location x along a pipe, where the wavelength λ of the acoustic waves to be measured is long compared to the diameter d of the pipe 12 (i.e., λ/d>>1), may be expressed as a superposition of a right traveling wave and a left traveling wave, as follows:

$$P(x,t)=(Ae^{-ik_r x}+Be^{+ik_l x})e^{i\omega t} \qquad \text{Eq. 1}$$

where A,B are the frequency-based complex amplitudes of the right and left traveling waves, respectively, x is the pressure measurement location along a pipe, ω is frequency (in rad/sec, where ω=2πf), and $k_r,k_l$ are wave numbers for the right and left travelling waves, respectively, which are defined as:

$$k_r \equiv \left(\frac{\omega}{a_{mix}}\right)\frac{1}{1+M_x} \text{ and } k_l \equiv \left(\frac{\omega}{a_{mix}}\right)\frac{1}{1-M_x} \qquad \text{Eq. 2}$$

where $a_{mix}$ is the speed of sound of the mixture in the pipe, ω is frequency (in rad/sec), and $M_x$ is the axial Mach number of the flow of the mixture within the pipe, where:

$$M_x \equiv \frac{V_{mix}}{a_{mix}} \qquad \text{Eq. 3}$$

where Vmix is the axial velocity of the mixture. For non-homogenous mixtures, the axial Mach number represents the average velocity of the mixture and the low frequency acoustic field description remains substantially unaltered.

The frequency domain representation P(x,ω) of the time-based acoustic pressure field P(x,t) within a pipe, is the coefficient of the $e^{i\omega t}$ term of Eq. 1, as follows:

$$P(x,\omega)=Ae^{-ik_r x}+Be^{+ik_l x} \qquad \text{Eq. 4}$$

Referring to FIG. 1, we have found that using Eq. 4 for P(x,ω) at three axially distributed pressure measurement locations $x_1,x_2,x_3$ along the pipe 12 leads to an equation for $a_{mix}$ as a function of the ratio of frequency based pressure measurements, which allows the coefficients A,B to be eliminated. For optimal results, A and B are substantially constant over the measurement time and substantially no sound (or acoustic energy) is created or destroyed in the measurement section. The acoustic excitation enters the test section only through the ends of the test section 51 and, thus, the speed of sound within the test section 51 can be measured independent of the acoustic environment outside of the test section. In particular, the frequency domain pressure measurements $P_1(\omega), P_2(\omega), P_3(\omega)$ at the three locations $x_1, x_2, x_3$, respectively, along the pipe 12 using Eq. 1 for right and left traveling waves are as follows:

$$P_1(\omega) = P(x=x_1, \omega) = Ae^{-ik_r x_1} + Be^{+ik_l x_1} \quad \text{Eq. 5}$$

$$P_2(\omega) = P(x=x_2, \omega) = Ae^{-ik_r x_2} + Be^{+ik_l x_2} \quad \text{Eq. 6}$$

$$P_3(\omega) = P(x=x_3, \omega) = Ae^{-ik_r x_3} + Be^{+ik_l x_3} \quad \text{Eq. 7}$$

where, for a given frequency, A and B are arbitrary constants describing the acoustic field between the sensors 14,16,18. Forming the ratio of $P_1(\omega)/P_2(\omega)$ from Eqns. 6,7, and solving for B/A, gives the following expression:

$$R \equiv \frac{B}{A} = \frac{e^{-ik_r x_1} - \left[\frac{P_1(\omega)}{P_2(\omega)}\right] e^{-ik_r x_2}}{\left[\frac{P_1(\omega)}{P_2(\omega)}\right] e^{ik_l x_2} - e^{ik_l x_1}} \quad \text{Eq. 8}$$

where R is defined as the reflection coefficient.

Forming the ratio of $P_1(\omega)/P_3(\omega)$ from Eqs. 5 and 7 and solving for zero gives:

$$\frac{e^{-ik_r x_1} + Re^{ik_l x_1}}{e^{-ik_r x_3} + Re^{ik_l x_3}} - \left[\frac{P_1(\omega)}{P_3(\omega)}\right] = 0 \quad \text{Eq. 9}$$

where R=B/A is defined by Eq. 8 and kr and kl are related to $a_{mix}$ as defined by Eq. 2. Eq. 9 may be solved numerically, for example, by defining an "error" or residual term as the magnitude of the left side of Eq. 9, and iterating to minimize the error term.

$$\text{mag}\left[\frac{e^{-ik_r x_1} + Re^{ik_l x_1}}{e^{-ik_r x_3} + Re^{ik_l x_3}} - \left[\frac{P_1(\omega)}{P_3(\omega)}\right]\right] \equiv \text{Error} \quad \text{Eq. 10}$$

For many applications in the oil industry, the axial velocity of the flow in the pipe is small compared to the speed of sound in the mixture (i.e., the axial Mach number $M_x$ is small compared to one). For example, the axial velocity of the oil $V_{oil}$ in a typical oil well is about 10 ft/sec and the speed of sound of oil $a_{oil}$ is about 4,000 ft/sec. Thus, the Mach number Mx of a pure oil mixture is 0.0025 ($V_{oil}/a_{oil}$= 10/4,000), and Eq. 2 reduces to approximately:

$$k_r = k_l = \frac{\omega}{a_{mix}} \quad \text{Eq. 11}$$

and the distinction between the wave numbers for the right and left traveling waves is eliminated. In that case (where Mx is negligible), since all of the variables in Eq. 10 are known except for $a_{mix}$, the value for $a_{mix}$ can be iteratively determined by evaluating the error term at a given frequency $\omega$ and varying $a_{mix}$ until the error term goes to zero. The value of $a_{mix}$ at which the magnitude of the error term equals zero (or is a minimum), corresponds to the correct value of the speed of sound of the mixture $a_{mix}$. As Eq. 10 is a function of frequency $\omega$, the speed of sound $a_{mix}$ at which the error goes to zero is the same for each frequency $\omega$ evaluated (discussed more hereinafter). However, in practice, there may be some variation over certain frequencies due to other effects, e.g., pipe modes, non-acoustical pressure perturbation, discretization errors, etc., which may be filtered, windowed, averaged, etc. if desired (discussed more hereinafter). Furthermore, since each frequency is an independent measurement of the same parameter, the multiple measurements may be weighted averaged or filtered to provide a single more robust measurement of the speed of sound.

One example of how the speed of sound of the mixture $a_{mix}$ in the pipe 12 may be used is to determine the volume fraction of the mixture. In particular, the speed of sound of a mixture $a_{mix}$ of two fluids (where a fluid is defined herein as a liquid or a gas) in a pipe is in general related to the volume fraction of the two fluids. This relationship may be determined experimentally or analytically. For example, the speed of sound of a mixture may be expressed as follows:

$$a_{mix} = \sqrt{\frac{1 + \frac{\rho_1}{\rho_2}\frac{h_2}{h_1}}{\frac{1}{a_1^2} + \frac{\rho_1}{\rho_2}\frac{h_2}{h_1}\frac{1}{a_2^2}}} \quad \text{Eq. 12}$$

where $a_1, a_2$ are the known speeds of sound, $\rho_1, \rho_2$ are the known densities, and $h_1, h_2$ are the volume fractions of the two respective fluids, $a_{mix}$ is the speed of sound of the mixture, and the densities $\rho_1, \rho_2$ of the two fluids are within about an order of magnitude (10:1) of each other. Other expressions relating the phase fraction to speed of sound may be used, being derived experimentally, analytically, or computationally.

Figure 2:
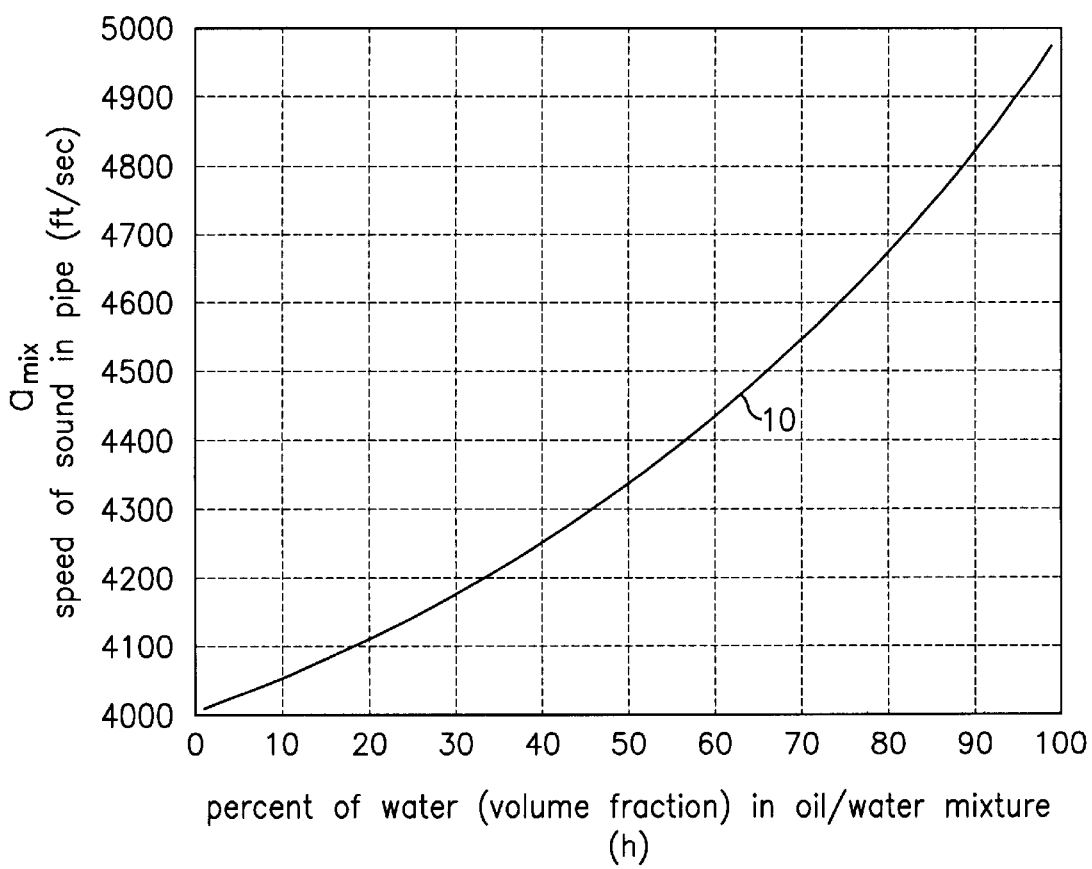
FIG. 2 is a graph of the speed of sound of a mixture versus the percent water volume fraction for an oil/water mixture, in accordance with the present invention.

Referring to FIG. 2, where the fluid is an oil/water mixture, a curve 10 shows the speed of sound of the mixture $a_{mix}$ plotted as a function of water volume fraction using Eq. 12. For this illustrative example, the values used for density ($\rho$) and speed of sound (a) of oil and water are as follows:

Density ($\rho$): $\rho_{water}$=1,000 kg/m$^3$; $\rho_{oil}$=700 kg/m$^3$

Speed of sound (a): $a_{water}$=5,000 ft/sec; $a_{oil}$=4,000 ft/sec.

The subscripts 1,2 of Eq. 12 assigned to the parameters for each fluid is arbitrary provided the notation used is consistent. Thus, if the speed of sound of the mixture $a_{mix}$ is measured, the oil/water fraction may be determined.

Figure 3:
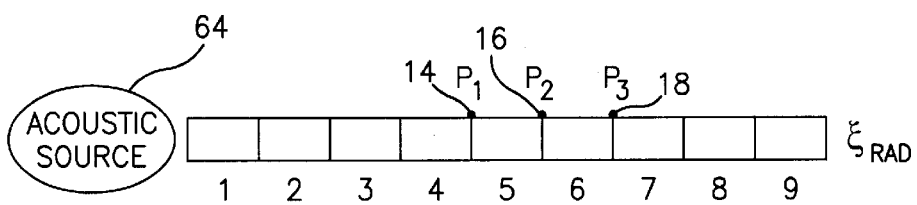
FIG. 3 is a transmission matrix model for the acoustics of an example pipe having 9 sections and a radiation impedance $\zeta_{rad}$, in accordance with the present invention.

Referring to FIG. 3, to illustrate the concept by example, a transmission matrix model for the acoustics of an example pipe having 9 sections (or elements or segments) 1–9, an acoustic source 64, a radiation (or transmission) impedance $\zeta_{rad}$ ($\zeta_{rad}$=$P/\rho_{mix} a_{mix} u_{mix}$) where $u_{mix}$ is an acoustic perturbation; Mx=0, and where the pressures $P_1, P_2, P_3$ are measured across test sections 5–6 and 6–7. For this example, each element is 1 meter long.

Depending on the application, an explicit acoustic noise source may or may not be required, as the background acoustic noises within the pipe may provide sufficient excitation to enable a speed of sound measurement from existing ambient acoustic pressures. In an oil or gas well application, if the background acoustic noises are not sufficient, an acoustic noise source (not shown) may be placed at the surface of the well or within the well, provided the source is acoustically coupled to the test section 51 over which the speed of sound is measured.

Figure 4:
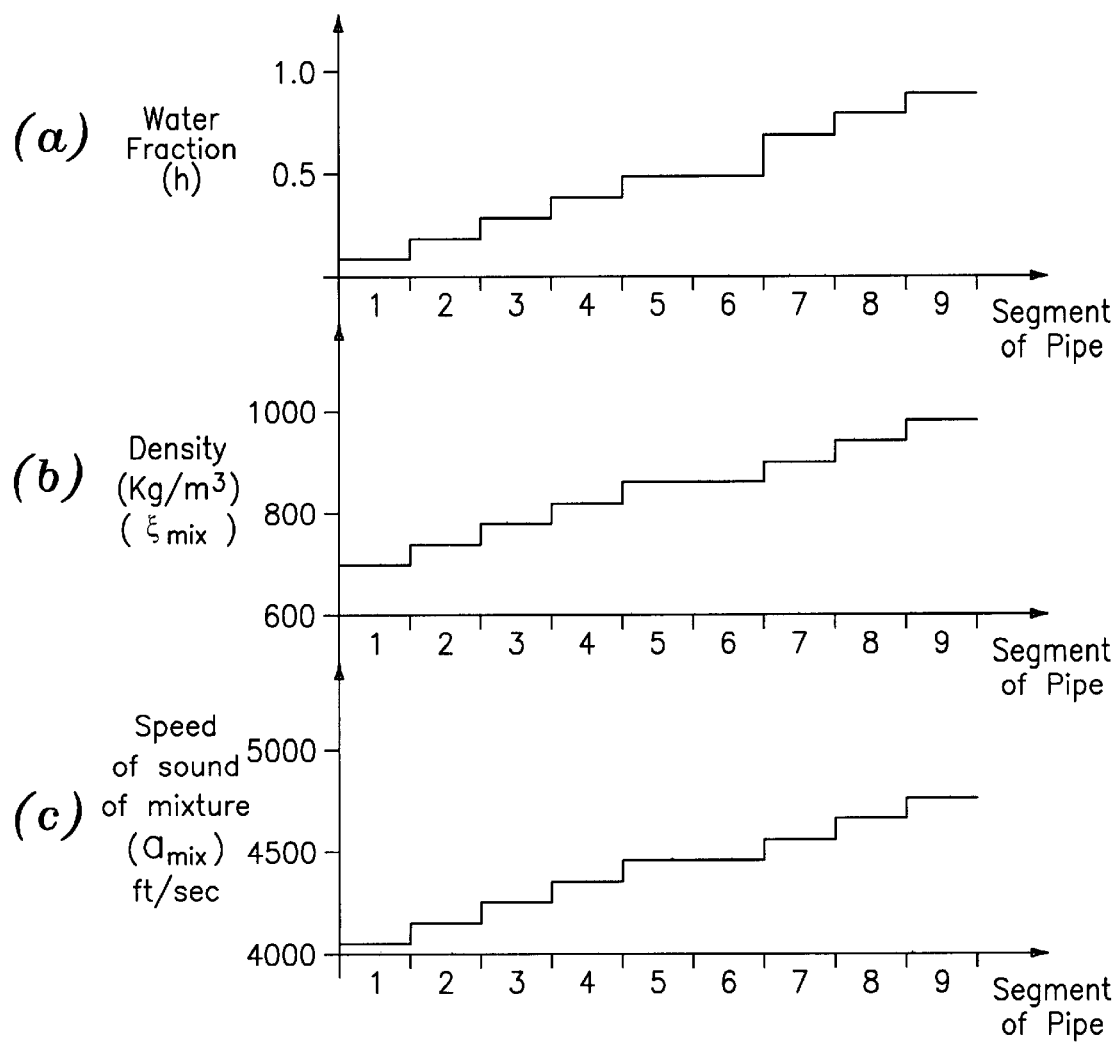
FIG. 4, illustrations (a)–(c), are graphs of axial values for $\rho_{mix}$, $a_{mix}$, $h_{water}$ properties of a mixture for the segments of the pipe of FIG. 3, in accordance with the present invention.
Figure 5:
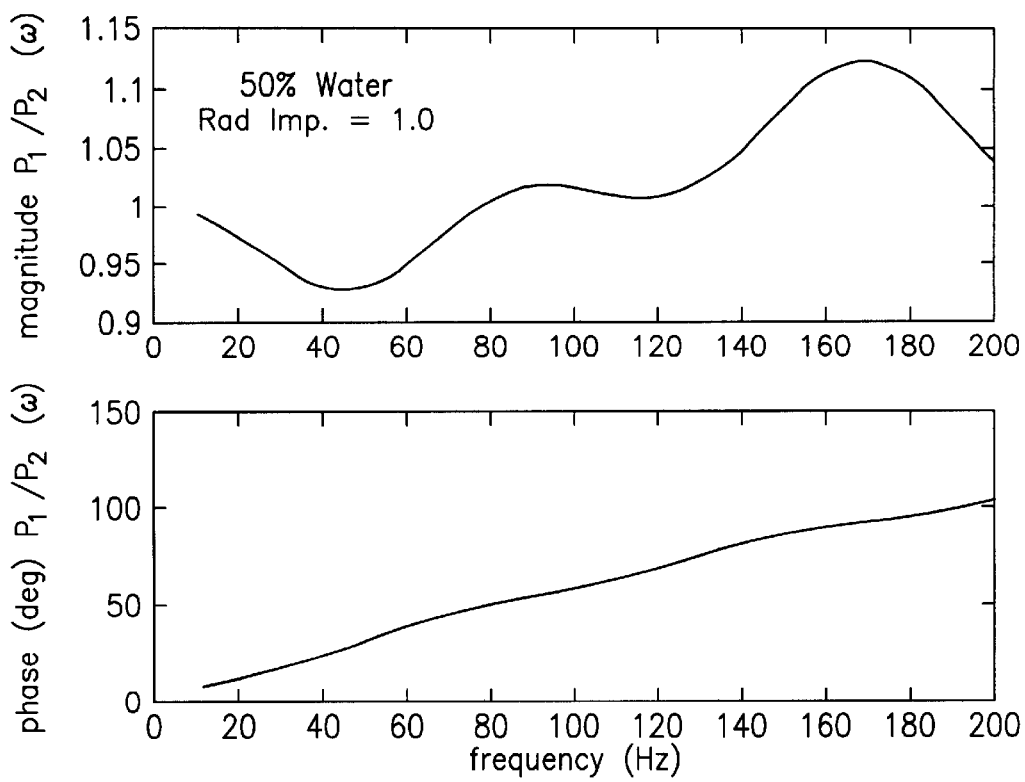
FIG. 5 is a graph of magnitude and phase versus frequency for a ratio of two pressures P1/P2, for radiation impedance of 1.0, water fraction of 50%, and axial properties of FIG. 4, in accordance with the present invention.
Figure 6:
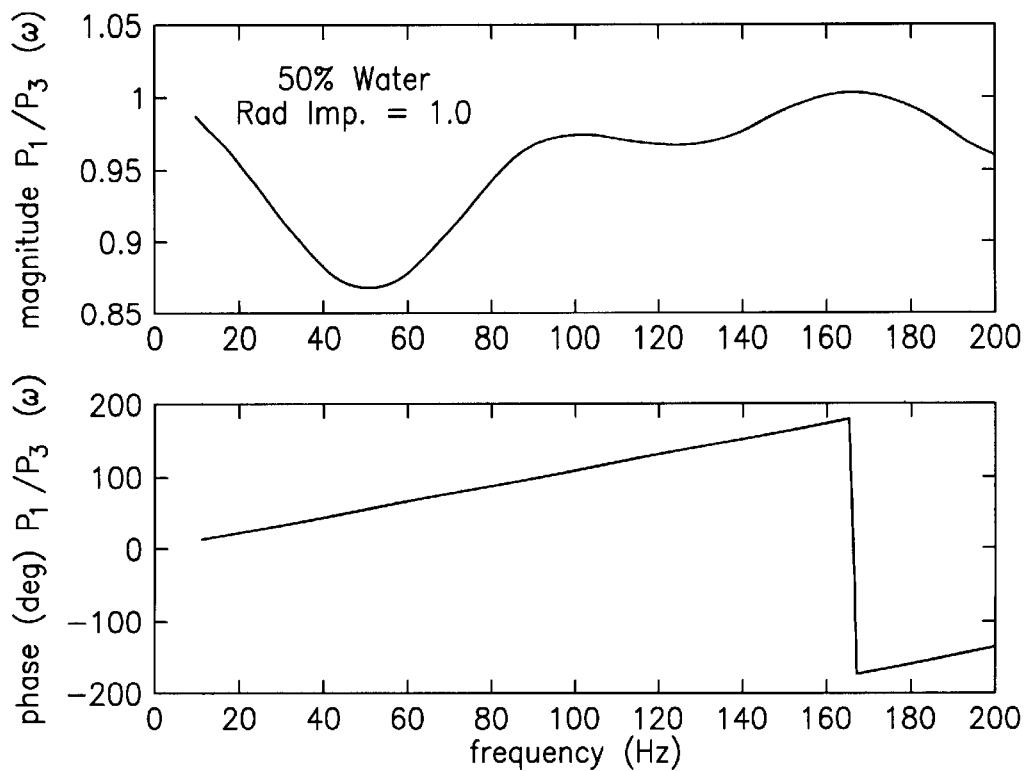
FIG. 6 is a graph of magnitude and phase versus frequency for a ratio of two pressures P1/P3, for radiation impedance of 1.0, water fraction of 50%, and axial properties of FIG. 4, in accordance with the present invention.

Referring to FIG. 4, illustrations (a)–(c), an example of the axial properties of the mixture in the segments 1–9 of the pipe 12 is shown. The volume fraction of water h, the speed of sound of the mixture $a_{mix}$, and the density of the mixture $\rho_{mix}$ vary over the length of the pipe 12 and the test segments 5,6 (from 4–6 meters) between the pressure measurements $P_1$–$P_3$ have constant properties. In particular, the values for $\rho_{mix}$, $a_{mix}$, $h_{water}$ for sections 1–9, respectively, are shown graphically in FIG. 4 and are as follows:

$h_{water}$=0.1, 0.2, 0.3, 0.4, 0.5, 0.6, 0.7, 0.8, 0.9;

$\rho_{mix}$=730, 760, 790, 820, 850, 850, 910, 940, 970 (kg/m³);

$a_{mix}$=4053, 4111, 4177, 4251, 4334, 4334, 4539, 4667, 4818 (ft/sec);

Referring to FIGS. 5,6, the magnitude and phase of the ratio of the frequency based pressure signals $P_1(\omega)/P_2(\omega)$ and $P_1(\omega)/P_3(\omega)$ is shown for the model of FIG. 3 with the properties of FIG. 4 with 50% water in the test section and a radiation impedance of $\zeta$rad=1.0 corresponding to an infinitely long pipe with constant properties of $\rho_{mix}$ and $a_{mix}$ for section 9 and beyond.

Figure 7:
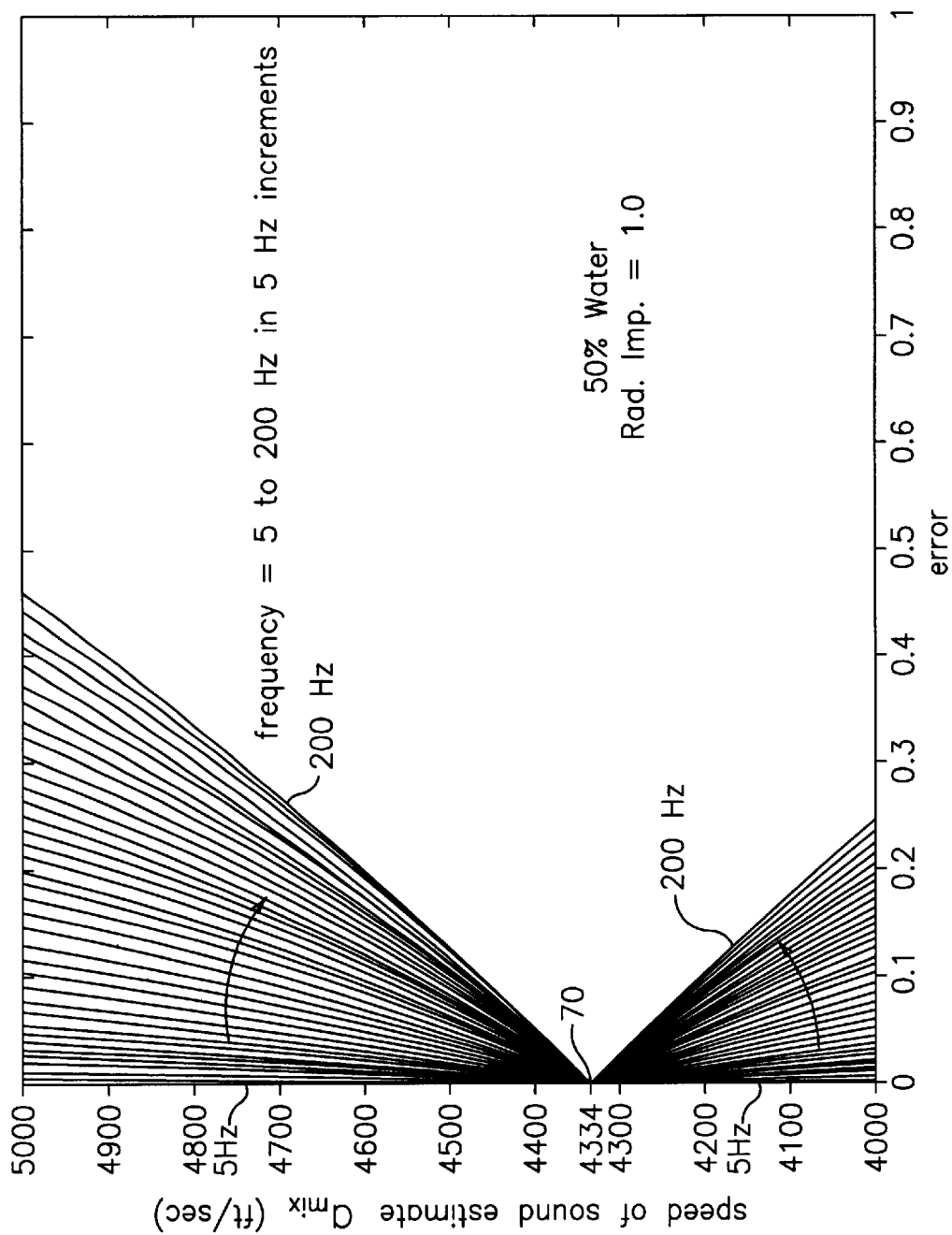
FIG. 7 is a graph of the magnitude of the speed of sound estimate versus an error term over a range of frequencies, using the frequency responses of FIGS. 5, 6, in accordance with the present invention.

Referring to FIG. 7, the error term of Eq. 10 using the frequency responses of FIGS. 5,6, is a family of curves, one curve for each frequency $\omega$, where the value of the error is evaluated for values of $a_{mix}$ varied from $a_{water}$ (5,000 ft/sec) to $a_{oil}$ (4,000 ft/sec) at each frequency and the frequency is varied from 5 to 200 Hz in 5 Hz increments. Other frequencies may be used if desired. The speed of sound $a_{mix}$ where the error goes to zero (or is minimized) is the same for each frequency o evaluated. In this case, the error is minimized at a point 70 when $a_{mix}$ is 4335 ft/sec. From FIG. 2, for an oil/water mixture, an $a_{mix}$ of 4335 ft/sec corresponds to a 50% water volume ratio in the test section which matches the water fraction of the model. Also, the sensitivity of a change in $a_{mix}$ to a change in error varies based on the evaluation frequency. Thus, the performance may be optimized by evaluating $a_{mix}$ at specific low sensitivity frequencies, such frequencies to be determined depending on the specific application and configuration.

Figure 8:
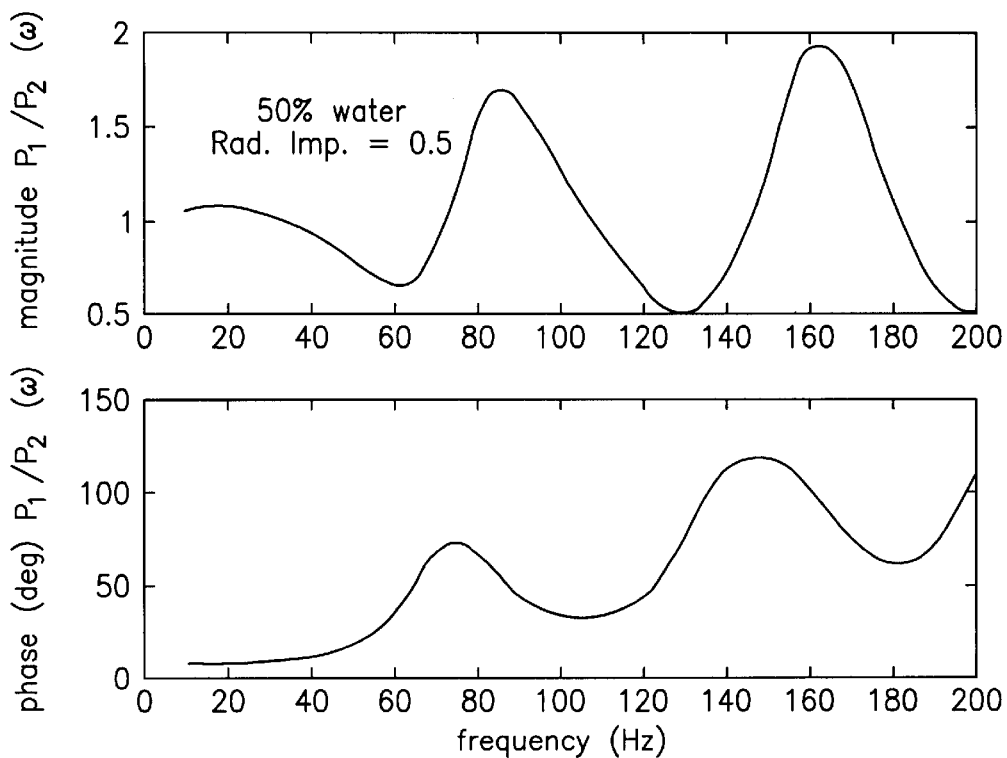
FIG. 8 is a graph of magnitude and phase versus frequency for a ratio of two pressures P1/P2, for radiation impedance of 0.5, water fraction of 50%, and constant axial properties of the mixture, in accordance with the present invention.
Figure 9:
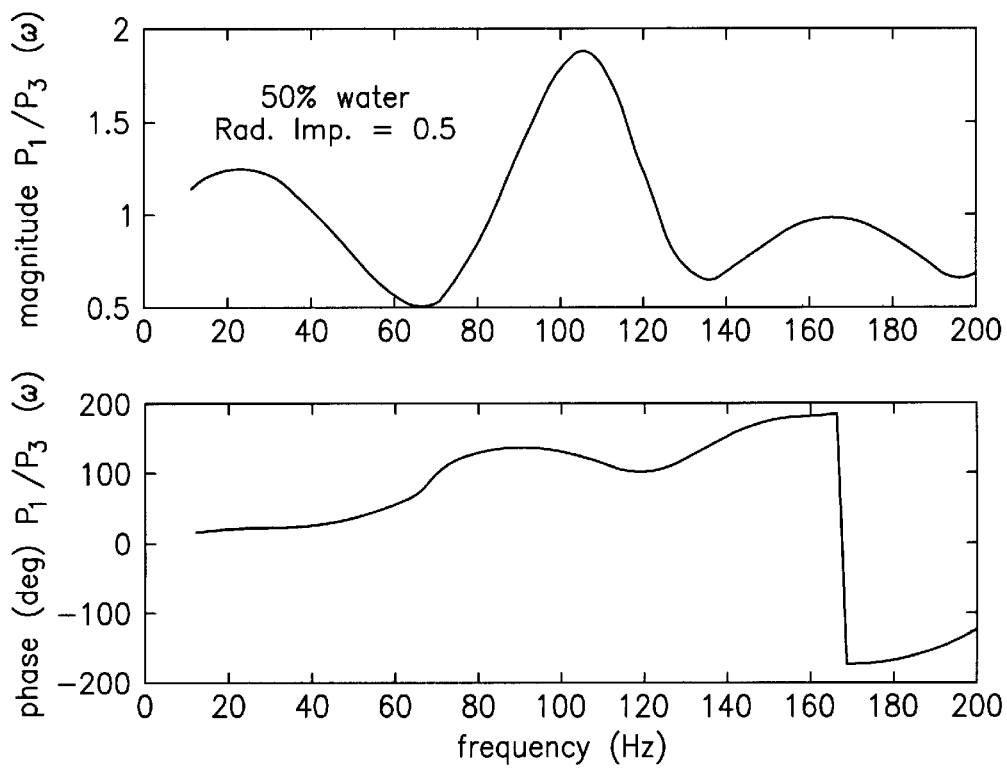
FIG. 9 is a graph of magnitude and phase versus frequency for a ratio of two pressures P1/P3, for radiation impedance of 0.5, water fraction of 50%, and constant axial properties of the mixture, in accordance with the present invention.

Referring to FIGS. 8,9, for an radiation impedance $\zeta$rad=0.5, the magnitude and phase of the frequency responses (i.e., the ratio of frequency based pressure signals) $P_1(\omega)/P_2(\omega)$ and $P_1(\omega)/P_3(\omega)$ is shown for the model of FIG. 3 with constant properties across all sections 1–9 of 50% water fraction (h=0.5), density of mixture $\rho_{mix}$=850 kg/m³, and speed of sound of mixture $a_{mix}$=4334 ft/sec.

Figure 12:
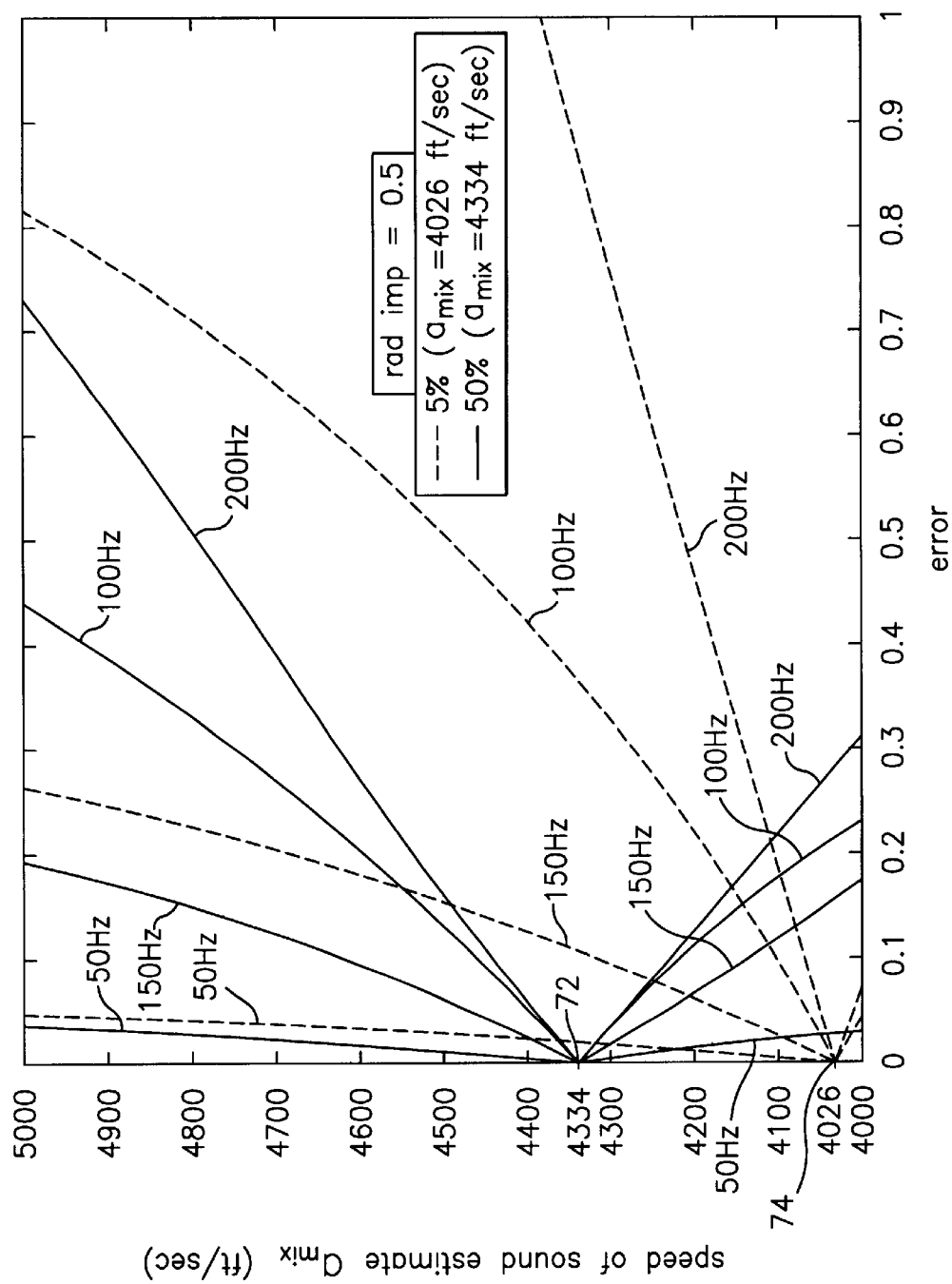
FIG. 12 is a graph of the magnitude of the speed of sound estimate versus an error term over a range of frequencies, using the frequency response for two different percent water fractions, of FIGS. 8–11, in accordance with the present invention.

Referring to FIG. 12, for a 50% water fraction, the magnitude of the error term of Eq. 10 using the frequency responses of FIGS. 8,9, is a family of curves, one curve for each frequency $\omega$, where the value of $a_{mix}$ is varied from $a_{water}$ (5,000 ft/sec) to $a_{oil}$ (4,000 ft/sec) at each frequency and is shown at four frequencies 50,100,150,200 Hz. As discussed hereinbefore, the speed of sound $a_{mix}$ where the error goes to zero (or is minimized) is the same for each frequency $\omega$ evaluated. In this case, the error is minimized at a point 72 where $a_{mix}$=4334 ft/sec, which matches the value of $a_{mix}$ shown in FIG. 7 for the same water fraction and different $\zeta$rad. From FIG. 2 (or Eq. 2), for an oil/water mixture, an $a_{mix}$ of 4334 ft/sec corresponds to a 50% water volume ratio in the test section which corresponds to the water fraction of the model. This shows that the invention will accurately determine $a_{mix}$ independent of the acoustic properties of the mixture outside the test sections and/or the termination impedances.

Figure 10:
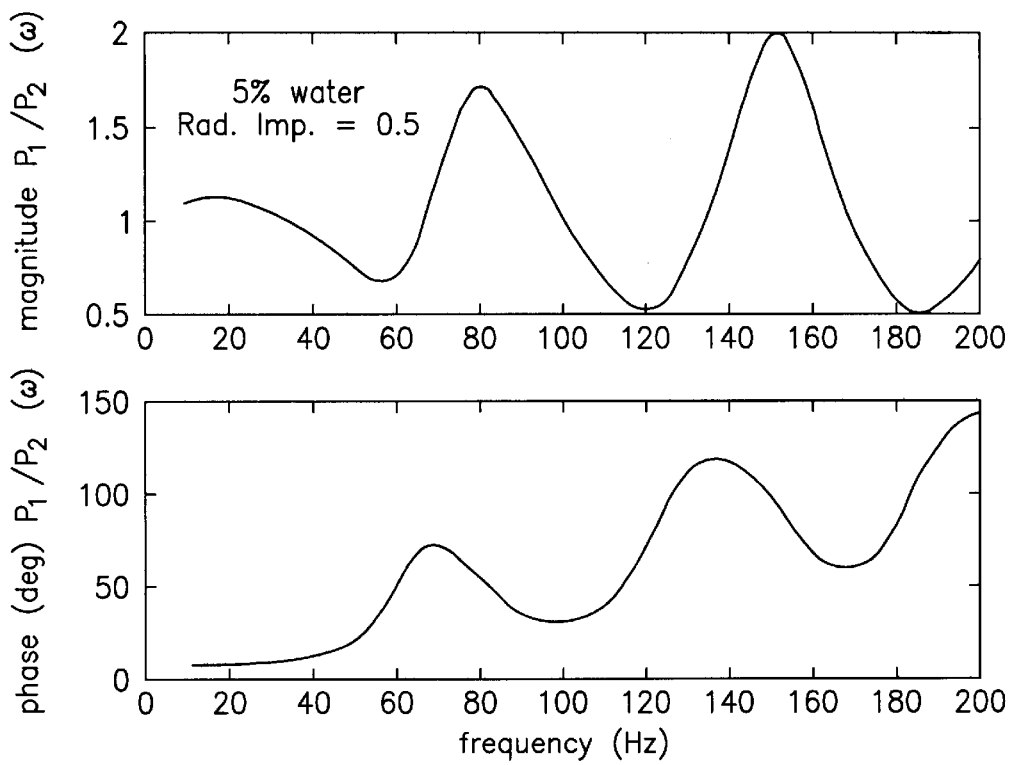
FIG. 10 is a graph of magnitude and phase versus frequency for a ratio of two pressures P1/P2, for radiation impedance of 0.5, water fraction of 5%, and constant axial properties of the mixture, in accordance with the present invention.
Figure 11:
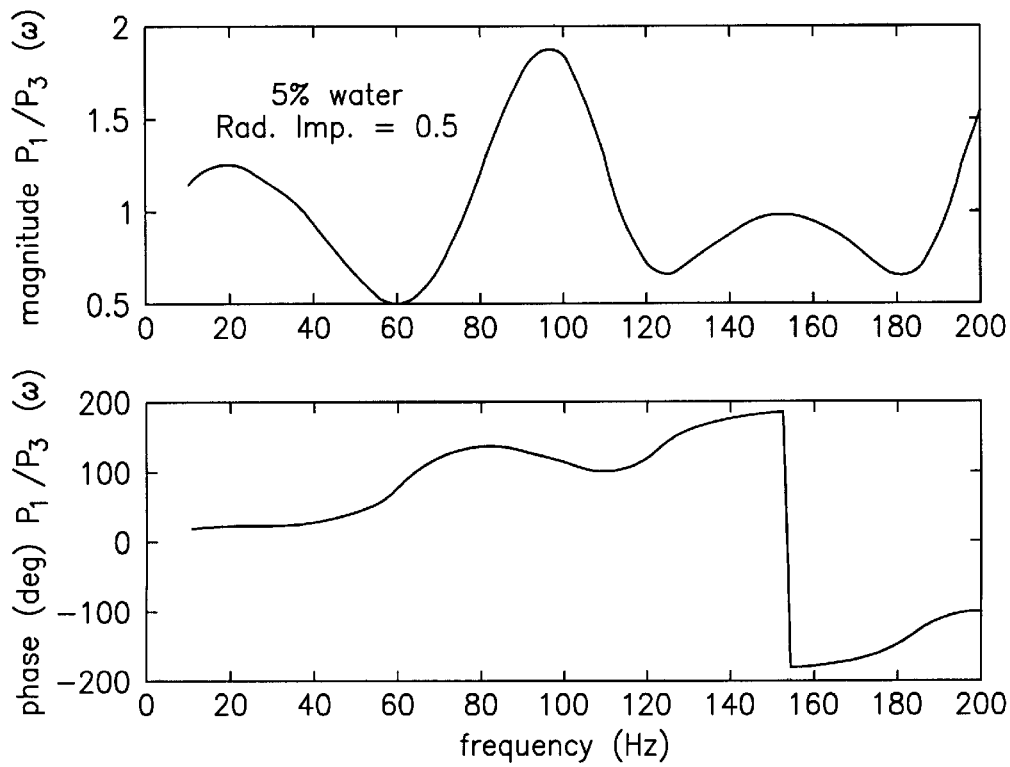
FIG. 11 is a graph of magnitude and phase versus frequency for a ratio of two pressures P1/P3, for radiation impedance of 0.5, water fraction of 5%, and constant axial properties of the mixture, in accordance with the present invention.

Referring to FIGS. 10,11, the magnitude and phase of the frequency responses (i.e., the ratio of the frequency based pressure signals) $P_1(\omega)/P_2(\omega)$ and $P_1(\omega)/P_3(\omega)$ is shown for the model of FIG. 3 with constant properties across all sections 1–9 of 5% water fraction (h=0.05), density of mixture $\rho_{mix}$=715 kg/m³, and speed of sound of mixture $a_{mix}$=4026 ft/sec, and a radiation impedance $\zeta$rad=0.5.

Referring to FIG. 12, for a 5% water fraction, the magnitude of the error term of Eq. 10 using the frequency responses of FIGS. 10,11, is a family of dashed curves, one curve for each frequency $\omega$, where the value of $a_{mix}$ is varied from $a_{water}$ (5,000 ft/sec) to $a_{oil}$ (4,000 ft/sec) at each frequency and is shown at four frequencies 50,100,150,200 Hz. As discussed hereinbefore, the speed of sound $a_{mix}$ where the error goes to zero (or is minimized) is the same for each frequency $\omega$ evaluated. In this case, the error is minimized at a point 74 when $a_{mix}$=4026 ft/sec. From FIG. 1 (or Eq. 1), for an oil/water mixture, an $a_{mix}$ of 4026 ft/sec corresponds to a 5% water volume ratio in the test section which corresponds to the water fraction of the model and, thus, verifies the results of the model.

Referring to FIG. 12, for both 5% and 50% water fraction, the sensitivity of a change in $a_{mix}$ to a change in error varies based on the evaluation frequency. In particular, for this example, of the four frequencies shown, the error approaches zero with the largest slope ($\Delta$Error/$\Delta a_{mix}$) for the 200 Hz curve, thereby making it easier to detect the value where the error goes to zero, and thus the value of $a_{mix}$. Thus, 200 Hz would likely be a robust frequency to use to determine the speed of sound in this example.

If the pressure sensors are equally spaced (i.e., x1–x2=x3–x2=$\Delta$x; or $\Delta$x1=$\Delta$x2=$\Delta$x) and the axial Mach number Mx is small compared to one (and thus, kr=kl=k), Eq. 10 may be solved for k (and thus $a_{mix}$) in a closed-form solution as a function of the pressure frequency responses (or frequency based signal ratios) as follows:

$$k = \frac{\omega}{a_{mix}} = \left[\frac{1}{\Delta x}\right] i \log\left[\frac{P_{12} + P_{13}P_{12} + (P_{12}^2 + 2P_{13}P_{12}^2 + P_{13}^2 P_{12}^2 - 4P_{13}^2)^{1/2}}{2P_{13}}\right] \quad \text{Eq. 13}$$

Solving for $a_{mix}$, gives:

$$a_{mix} = \frac{\omega}{\left[\frac{1}{\Delta x}\right] i \log\left[\frac{P_{12} + P_{13}P_{12} + (P_{12}^2 + 2P_{13}P_{12}^2 + P_{13}^2 P_{12}^2 - 4P_{13}^2)^{1/2}}{2P_{13}}\right]} \quad \text{Eq. 14}$$

where $P_{12}$=$P_1(\omega)/P_2(\omega)$, $P_{13}$=$P_1(\omega)/P_3(\omega)$, is the square root of −1, and the result of the Log[ ] function is an imaginary number, yielding a real number for the speed of sound $a_{mix}$.

The analytical solution to the Eq. 10 shown in Eqs. 13 and 14 is valid primarily for the frequencies for which the length of the test section 51 along the pipe 12 (i.e., x3–x1 or 2$\Delta$x for equally spaced sensors) is shorter than the wavelength $\lambda$ of the acoustic waves to be measured. This restriction is due to multiple possible solutions to the Eq. 10. Alternative solutions to Eq. 10 for other frequency ranges may be derived using a variety of known techniques.

An alternative closed form solution for $a_{mix}$ (in a trigonometric form) from the three pressure Eqs. 5–7, where the pressure sensors are equally spaced and Mx is negligible (i.e, kl=kr), is as follows. Forming the ratio $[P_1(\omega)+P_3(\omega)]/P_2(\omega)$ from Eqs. 5–7, gives the following expression:

$$\frac{P_1(\omega) + P_3(\omega)}{P_2(\omega)} = \frac{Ae^{-ikx_1} + Be^{+ikx_1} + Ae^{-ikx_3} + Be^{+ikx_3}}{Ae^{-ikx_2} + Be^{+ikx_2}} \quad \text{Eq. 15}$$

For equally spaced sensors, x1=0,x2=$\Delta$x, x3=2$\Delta$x (x1=0 for convenience only), which gives:

$$\frac{P_1(\omega) + P_3(\omega)}{P_2(\omega)} = \frac{A + B + Ae^{-2ik\Delta x} + Be^{+2ik\Delta x}}{Ae^{-ik\Delta x} + Be^{+ik\Delta x}} \quad \text{Eq. 16}$$

Dividing the numerator and denominator by A, gives:

$$\frac{P_1(\omega) + P_3(\omega)}{P_2(\omega)} = \frac{1 + R + e^{-2ik\Delta x} + Re^{+2ik\Delta x}}{e^{-ik\Delta x} + Re^{+ik\Delta x}} \qquad \text{Eq. 17}$$

where R=B/A is defined by Eq. 8 with x1=0,x2=Δx, which gives:

$$R \equiv \frac{B}{A} = \frac{1 - \left[\frac{P_1(\omega)}{P_2(\omega)}\right]e^{-ik\Delta x}}{\left[\frac{P_1(\omega)}{P_2(\omega)}\right]e^{ik\Delta x} - 1} \qquad \text{Eq. 18}$$

Plugging R into Eq. 17, gives:

$$\frac{P_1(\omega) + P_3(\omega)}{P_2(\omega)} = \frac{1 + e^{-2ik\Delta x} + \left[\frac{1 - \left[\frac{P_1(\omega)}{P_2(\omega)}\right]e^{-ik\Delta x}}{\left[\frac{P_1(\omega)}{P_2(\omega)}\right]e^{ik\Delta x} - 1}\right](1 + e^{+2ik\Delta x})}{e^{-ik\Delta x} + \left[\frac{1 - \left[\frac{P_1(\omega)}{P_2(\omega)}\right]e^{-ik\Delta x}}{\left[\frac{P_1(\omega)}{P_2(\omega)}\right]e^{ik\Delta x} - 1}\right]e^{+ik\Delta x}} \qquad \text{Eq. 19}$$

Simplifying Eq. 19, gives:

$$\frac{P_1(\omega) + P_3(\omega)}{P_2(\omega)} = \frac{\left(\frac{P_1}{P_2} e^{+ik\Delta x} - 1\right)(1 + e^{-2ik\Delta x}) + \left(1 - \frac{P_1}{P_2} e^{-ikx}\right)(1 + e^{+2ik\Delta x})}{\left(\frac{P_1}{P_2} e^{+ik\Delta x} - 1\right)(e^{-ik\Delta x}) + \left(1 - \frac{P_1}{P_2} e^{-ikx}\right)(e^{+ik\Delta x})} \qquad \text{Eq. 20}$$

Distributing terms and simplifying, gives:

$$\frac{P_1(\omega) + P_3(\omega)}{P_2(\omega)} = \frac{-e^{-2ik\Delta x} + e^{+2ik\Delta x}}{-e^{-ik\Delta x} + e^{+ik\Delta x}} \qquad \text{Eq. 21}$$

Using the relation between exponents and the sine function, gives:

$$\frac{P_1(\omega) + P_3(\omega)}{P_2(\omega)} = \frac{2i\sin(2k\Delta x)}{2i\sin(k\Delta x)} = \frac{2\sin(kx)\cos(kx)}{\sin(kx)} \qquad \text{Eq. 22}$$

Simplifying and substituting $k = \omega/a_{mix}$, gives:

$$\frac{P_1(\omega) + P_3(\omega)}{P_2(\omega)} = 2\cos(k\Delta x) = 2\cos\left(\frac{\omega \Delta x}{a_{\min}}\right) \qquad \text{Eq. 23}$$

Eq. 23 is particularly useful due to its simple geometric form, from which $a_{mix}$ can be easily interpreted. In particular, $a_{mix}$ can be determined directly by inspection from a digital signal analyzer (or other similar instrument) set up to provide a display indicative of the left side of Eq. 23, which will be a cosine curve from which $a_{mix}$ may be readily obtained. For example, at the zero crossing of the cosine wave, Eq. 23 will be equal to zero and $a_{mix}$ will be equal to 2ωΔX/π. Alternatively, Eq. 23 may be used to determine amix using an iterative approach where a measured function is calculated from the left side of Eq. 23 (using the measured pressures) and compared to a cosine curve of the right side of Eq. 23 where amix is varied until it substantially matches the measured function. Various other curve fitting, parameter identification, and/or minimum error or solution techniques may be used to determine the value of amix that provides the best fit to satisfy Eq. 23.

Solving Eq. 23 for $a_{mix}$, gives the following closed-form solution:

$$a_{\min} = \frac{\omega \Delta x}{\cos^{-1}\left(\frac{P_1(\omega) + P_3(\omega)}{2P_2(\omega)}\right)} \qquad \text{Eq. 24}$$

$$= \frac{\omega \Delta x}{\cos^{-1}\frac{1}{2}\left(\frac{P_1(\omega)}{P_2(\omega)} + \frac{P_3(\omega)}{P_2(\omega)}\right)}$$

Figure 41:
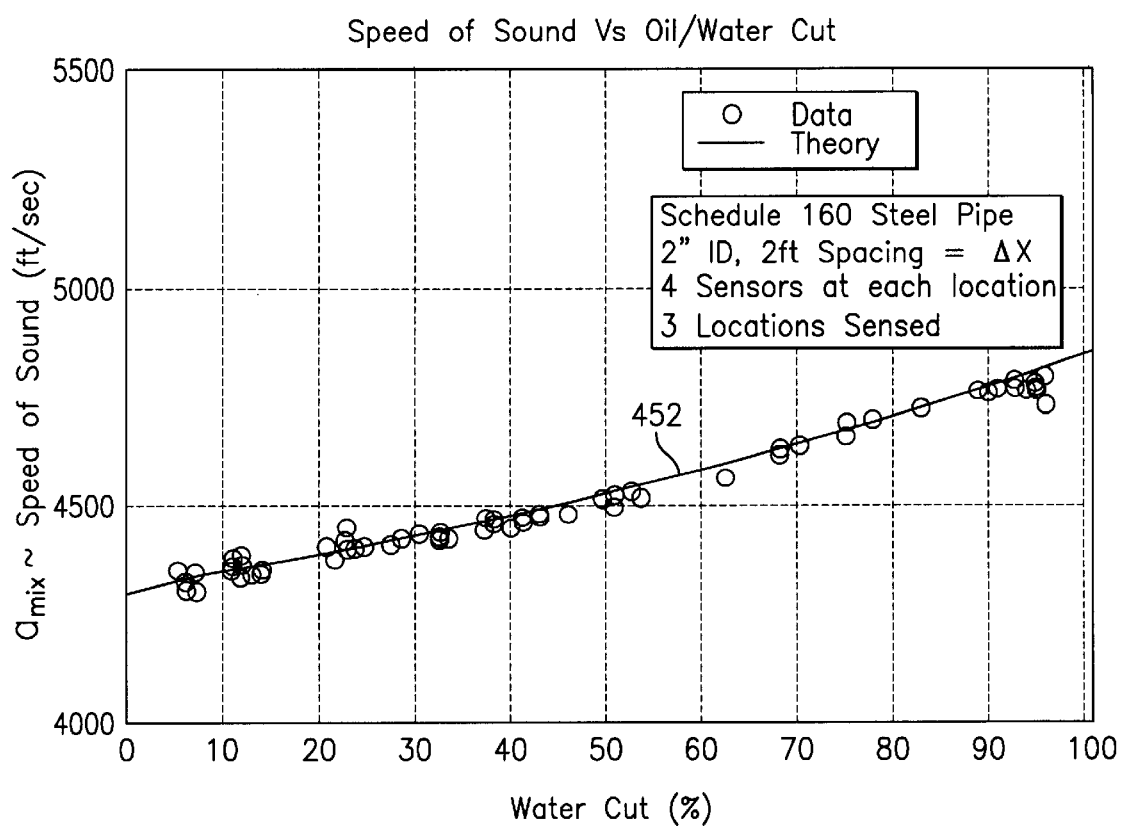
FIG. 41 is a graph of speed of sound versus water cut, in accordance with the present invention.

Referring to FIG. 41, a graph of speed of sound ($a_{mix}$) versus water cut is shown where $a_{mix}$ is calculated using Eq. 23 as described hereinbefore. FIG. 41 is for a Schedule 160 steel pipe having a 2 inch ID, Δx=2ft even spacing between three axial sensing locations, each sensor being a piezoelectric ac pressure sensor, there being four evenly circumferentially spaced sensors at each axial sensing location. The line 452 shows the theoretical value for water cut based on Eq. 12 and FIG. 2 discussed hereinbefore, and the circles are the calculated values for $a_{mix}$.

Alternatively, Eq. 9 may be written in trigonometric form for arbitrary spacing between the pressure sensors and where Mx is negligible (kl=kr), as follows:

$$\sin\left(\frac{\omega}{a_{mix}}(x_3 - x_1)\right) - \qquad \text{Eq. 25}$$

$$P_{32}\sin\left(\frac{\omega}{a_{mix}}(x_2 - x_1)\right) - P_{12}\sin\left(\frac{\omega}{a_{mix}}(x_3 - x_2)\right) = 0$$

where $P_{32} = P_3(\omega)/P_2(\omega)$ and $P_{12} = P_1(\omega)/P_2(\omega)$.

Figure 13:
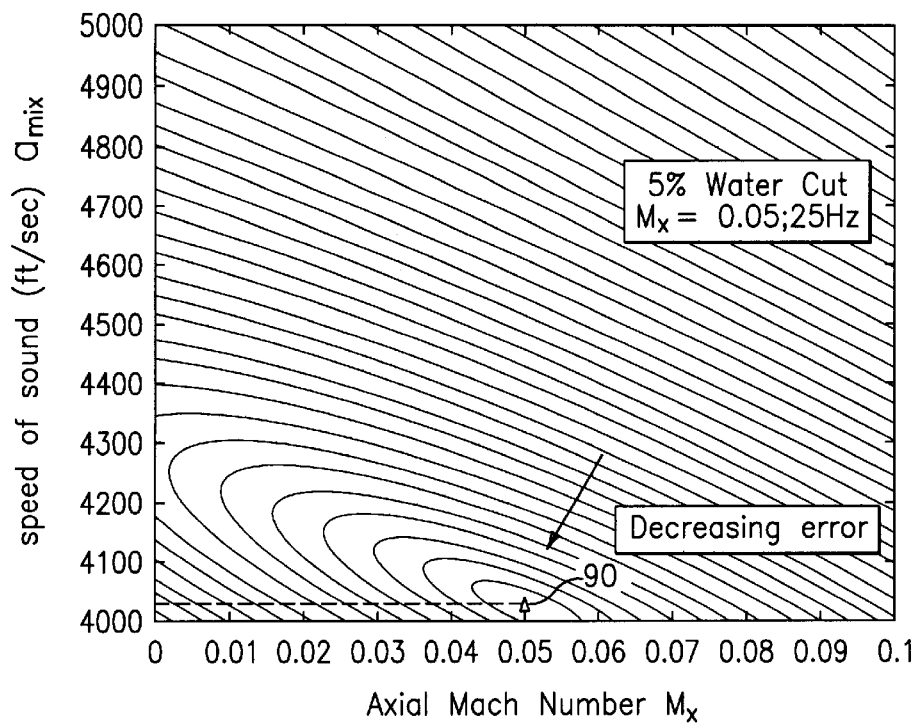
FIG. 13 is a contour plot of speed of sound versus axial Mach versus an error term, for 5% water fraction, Mach number of 0.05, at 25 Hz, in accordance with the present invention.
Figure 14:
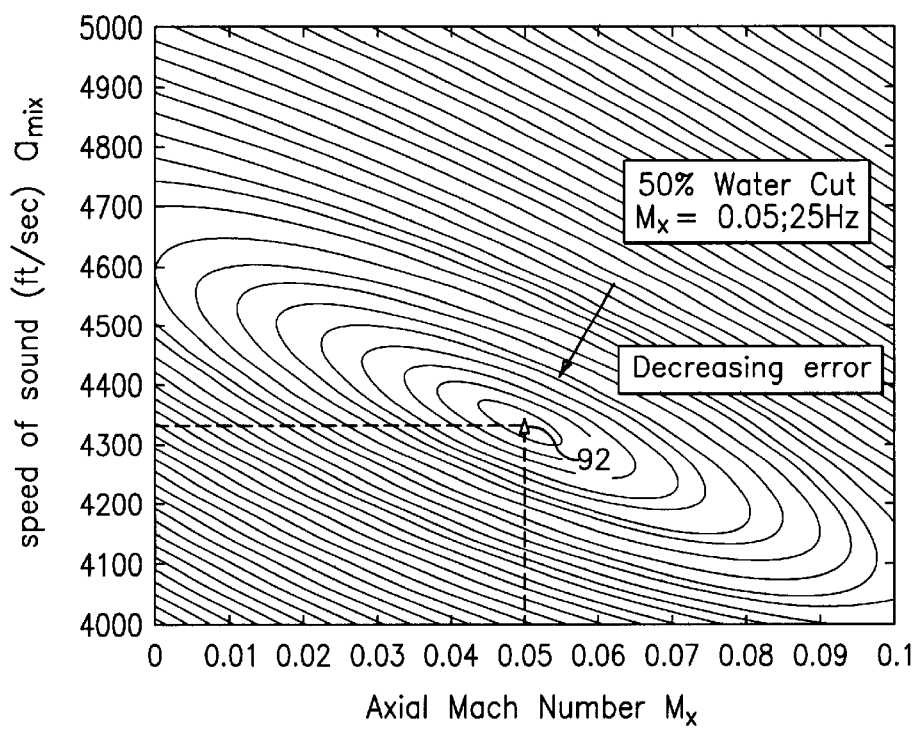
FIG. 14 is a contour plot of speed of sound versus axial Mach versus an error term, for 50% water fraction, Mach number of 0.05, at 25 Hz, in accordance with the present invention.

Referring to FIGS. 13,14, if Mach number Mx is not negligible and/or is desired to be calculated, the value of Mx and $a_{mix}$ where the error term of Eq. 10 is zero can be uniquely determined from Eq. 10 for a given water fraction. In particular, for a given % water fraction, there is a unique value indicated by points 90,92 for 5% and 50% water cut, respectively. Known software search algorithms may be used to vary $a_{mix}$ and Mx over predetermined ranges to find the value of Mx and $a_{mix}$ where the error=0 (discussed more hereinafter).

Figure 15:
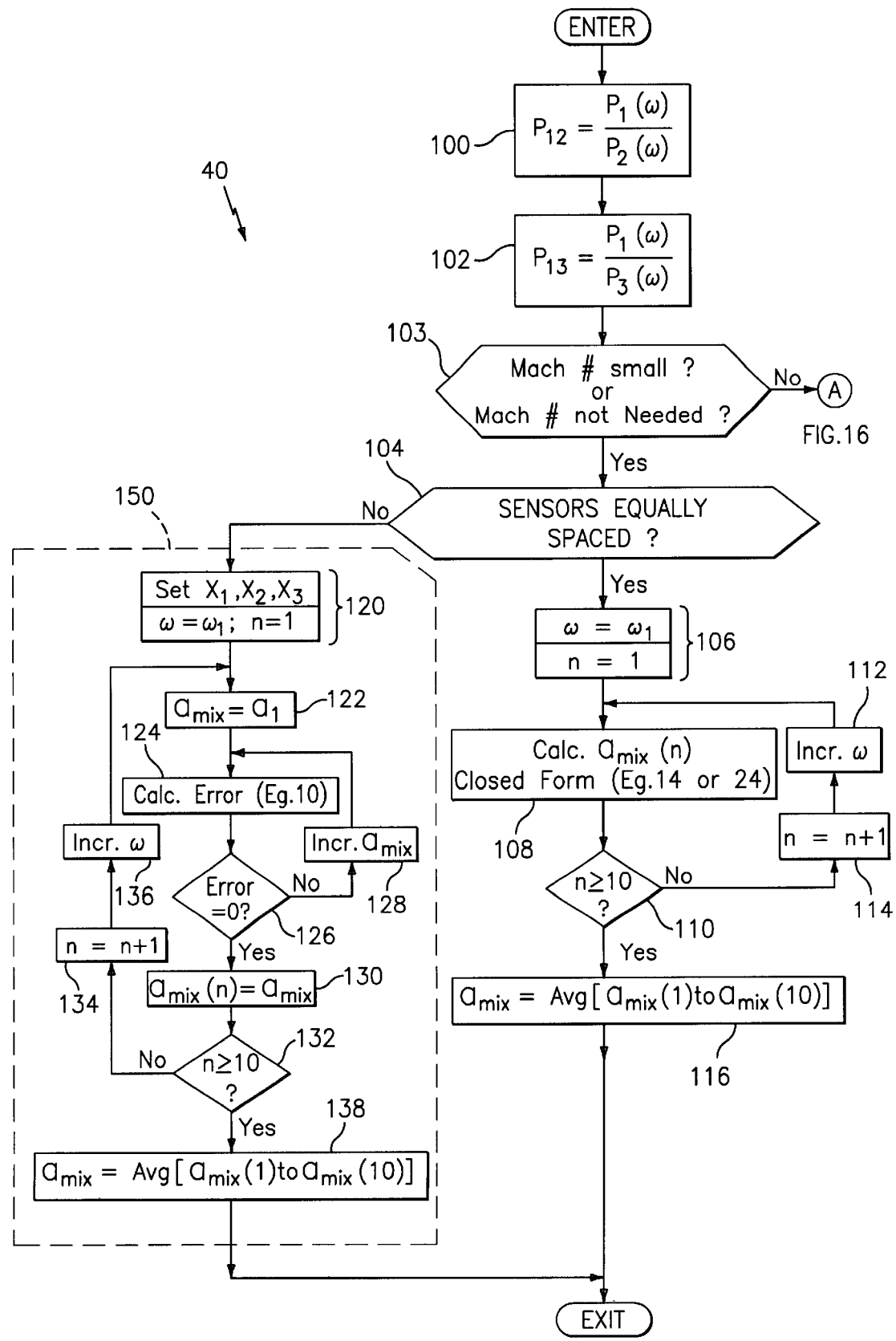
FIG. 15 is a portion of a logic flow diagram for logic of FIG. 1, in accordance with the present invention.

Referring to FIG. 15, the calculation logic 40 begins at a step 100 where $P_{12}$ is calculated as the ratio of $P_1(\omega)/P_2(\omega)$, and a step 102 where $P_{13}$ is calculated as the ratio of $P_1(\omega)/P_3(\omega)$. Next a step 103 determines whether the Mach number Mx of the mixture is negligible (or whether it is desirable to calculate Mx, i.e. for cases where Mx is not negligible, as set forth herein below with reference to "A" and FIG. 16). If Mx is negligible, a step 104 determines if the sensors 14,16,18 are equally spaced (i.e., x1-x2=x2-x3=Δx). If equally spaced sensors, steps 106 set initial values for ω=ω1 (e.g., 100 Hz) and a counter n=1. Next, a step 108 calculates $a_{mix}$(n) from the closed form solution of Eq. 14. Then, a step 110 checks whether the logic 40 has calculated $a_{mix}$ at a predetermined number of frequencies, e.g., 10. If n is not greater than 10, steps 112,114, increments the counter n by one and increases the frequency ω by a predetermined amount (e.g., 10 Hz) and the step 108 is repeated. If the logic 40 has calculated $a_{mix}$ at 10 frequencies, the result of the step 116 would be yes and the logic 40 goes to a step 116 which determines an average value for $a_{mix}$ using the values of $a_{mix}$ (n) over the 10 frequencies, and the logic 40 exits.

If the sensors are not equally spaced, a series of steps 150 are performed starting with steps 120 set x1,x2,x3 to the current pressure sensor spacing, and set initial values for $\omega=\omega 1$ (e.g., 100 Hz) and the counter n=1. Next, a step 122 sets $a_{mix}=a_{mix-min}$ (e.g., $a_{oil}$=4000 ft/sec) and a step 124 calculates the error term from Eq. 10. Then, a step 126 checks whether error=0. If the error does not equal zero, $a_{mix}$ is incremented by a predetermined amount in step 128 and the logic 40 goes back to step 124.

If the error=0 (or a minimum) in step 126, a step 130 sets $a_{mix}(n)=a_{mix}$. Next, a step 132 checks whether n is greater than or equal to 10. If not, a step 134 increments n by one and a step 136 increases the frequency $\omega$ by a predetermined amount (e.g., 10 Hz) and continues at step 122 as shown in FIG. 15. If n is greater than or equal to 10, a step 138 calculates an average value for $a_{mix}$ over the 10 frequencies, and the logic 40 ends.

Figure 16:
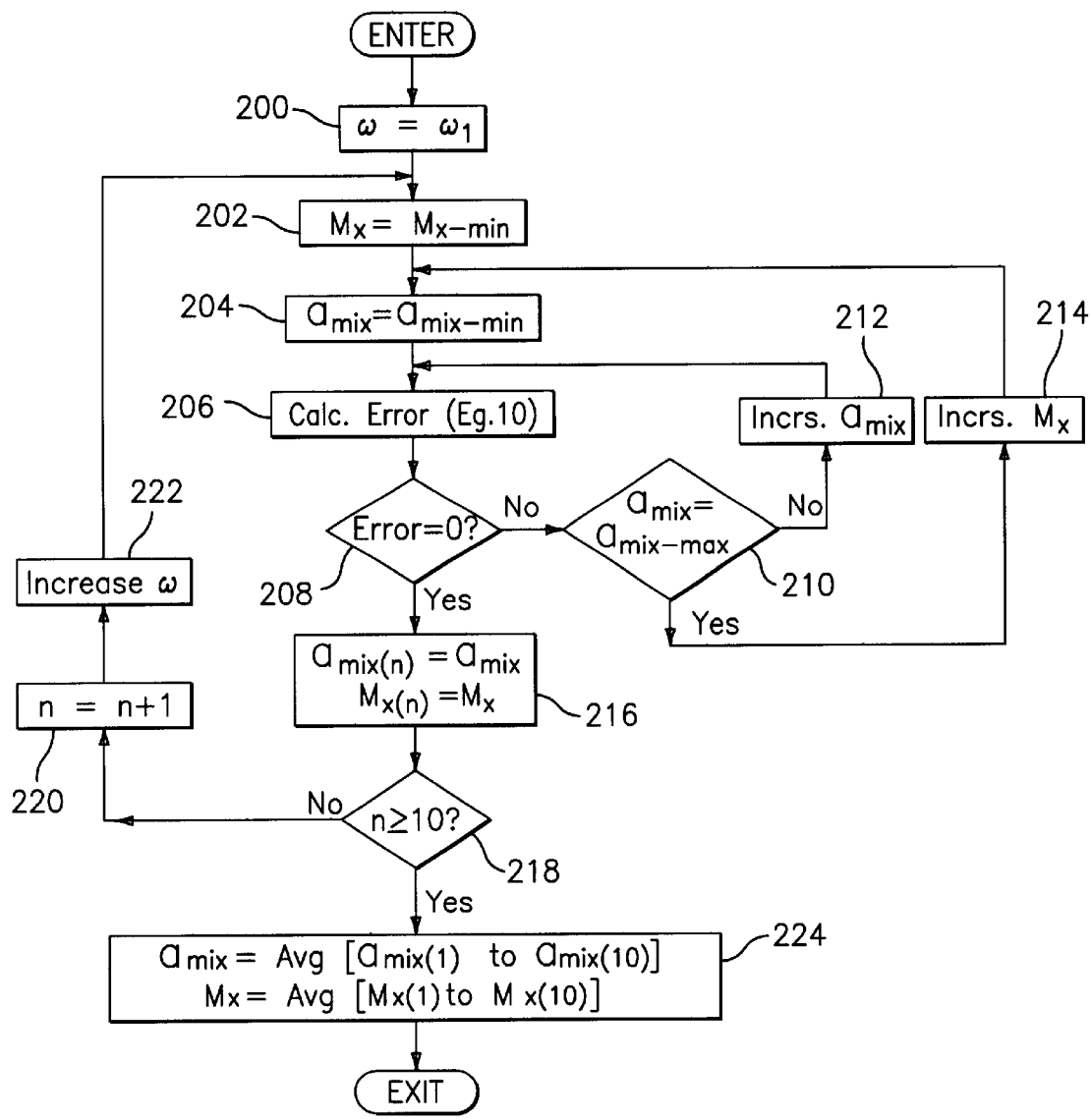
FIG. 16 is a continuation of the logic flow diagram of FIG. 15, in accordance with the present invention.

Referring to FIG. 16, if the Mach number Mx is not negligible, steps 200, 202, 204 sets initial conditions: $\omega=\omega 1$ (e.g., 100 Hz); Mx=Mx-min (e.g., 0); $a_{mix}=a_{mix-min}$ (e.g., $a_{oil}$=4000 ft/sec). Then, a step 206 calculates the error term of Eq. 10 at a step 202. Next, a step 208 checks whether the error=0 (or a minimum). If not, a step 210 checks whether $a_{mix}=a_{mix-mix}$ (e.g., $a_{water}$=5000 ft/sec).

If the result of step 210 is no, a step 212 increases $a_{mix}$ by a predetermined amount (e.g., 1 ft/sec) and the logic goes back to step 206. If the result of step 210 is yes, a step 214 increases Mx by a predetermined amount (e.g., 1) and the logic goes back to step 204.

When step 208 indicates erro=0 (or a minimum), a step 216 sets $a_{mix}(n)=a_{mix}$ and Mx(n)=Mx, and a step 218 checks whether the values of $a_{mix}$ and Mx have been calculated at 10 different frequencies. If not, a step 220 increments the counter n by one and a step 222 increases the value of the frequency $\omega$ by a predetermined amount (e.g., 10 Hz), and the logic goes back to step 202. If the values of $a_{mix}$ and Mx have been calculated at 10 different frequencies (i.e., n is equal to 10), a step 224 calculates a average values for $a_{mix}(n)$ and Mx(n) at the 10 different frequencies to calculate $a_{mix}$ and Mx, and the logic exists. The value for $a_{mix}$ above is similar to that shown in FIGS. 13,14, discussed hereinbefore, where the final value of $a_{mix}$ are the points 90,92 where the error equals zero.

Instead of calculating an average value for $a_{mix}$ in steps 116,138, 224, $a_{mix}$ may be calculated by filtering or windowing $a_{mix}(n)$, from predetermined frequencies. The number of frequencies and the frequencies evaluated may be any desired number and values. Also, instead of calculating $a_{mix}$ and/or Mx at more than one frequency, it may be calculated at only one frequency. Further, the logic shown in FIGS. 15,16 is one of many possible algorithms to calculate $a_{mix}$ using the teachings herein.

Figure 18:
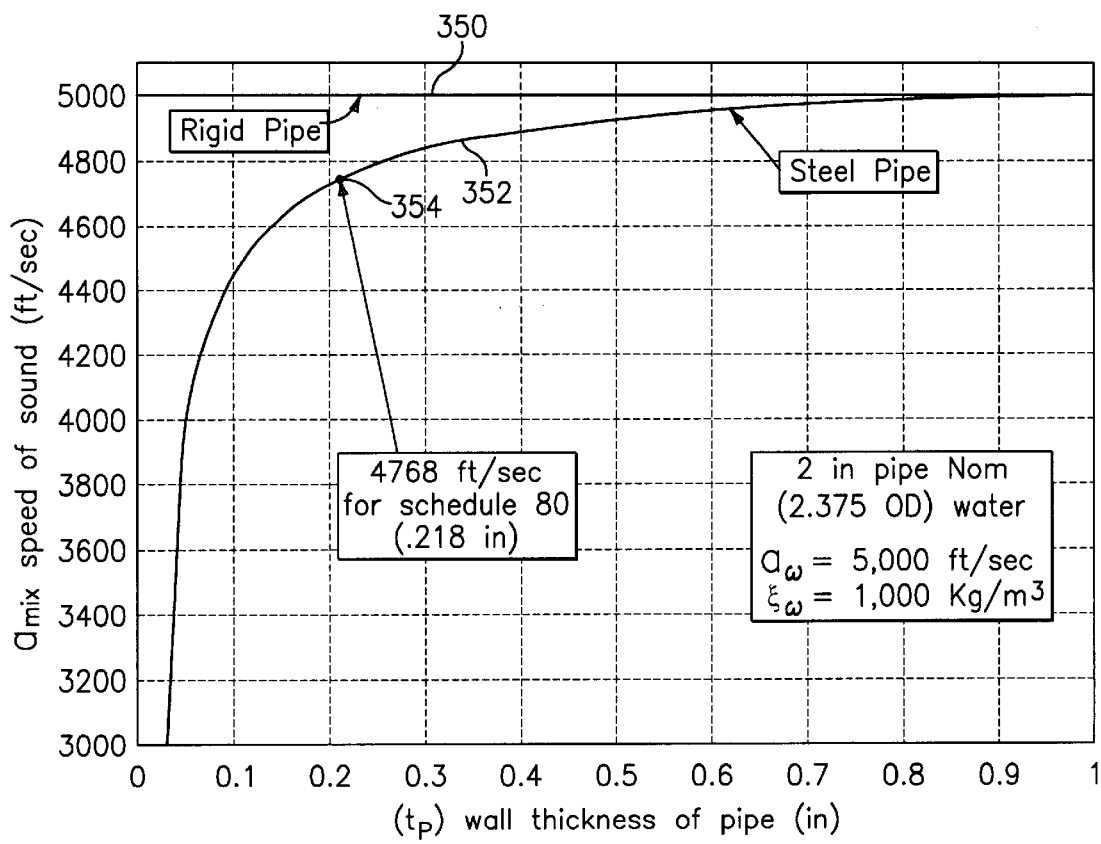
FIG. 18 is a plot of speed of sound against wall thickness of a pipe for a rigid and a non-rigid pipe, in accordance with the present invention.

Referring to FIGS. 1 and 18, the compliance (or flexibility) of the pipe 12 (or conduit) in the sensing region may influence the accuracy or interpretation of the measured speed of sound $a_{mix}$ of the mixture in two primary ways.

Regarding the first way, referring to FIG. 18, flexing of the pipe 12 in the sensing region reduces the measured speed of sound $a_{mix}$ from the sound in an unbounded domain. The sound speed in an unbounded domain (infinite media) is a property that is closely linked with the fluid properties. In particular, the influence of pipe wall thickness (or compliance of the pipe) on measured speed of sound due reduction in the speed of sound for a pipe having a 2 inch nominal diameter and having 100% water ($\rho_w$=1,000 kg/m$^3$; $a_w$=5,000 ft/sec) inside the pipe and a vacuum (or air) outside the pipe diameter, is shown. The speed of sound of water in an infinitely rigid pipe (i.e., infinite modulus) is indicated by a flat curve 350, and the speed of sound of water in a steel pipe is indicated by a curve 352. A point 354 on the curve 352 indicates the value of the speed of sound of about 4768 ft/sec for a Schedule 80 steel pipe. Accordingly, the thicker the pipe wall, the closer the speed of sound approaches the value of 5,000 ft/sec for an infinitely rigid pipe.

The errors (or boundary effects) shown in FIG. 18 introduced into the measurements by a non-rigid (or compliant) pipe 12 can be calibrated and corrected for to accurately determine the speed of sound in the fluid in an unbounded media. Thus, in this case, while the system (pipe) does modify the propagation velocity, such velocity can be mapped to the propagation velocity in an infinite media in a predictable fashion.

In particular, for fluids contained in a compliant pipe, the propagation velocity of compression waves is influenced by the structural properties of the pipe. For a fluid contained in the pipe 12 surrounded with a fluid of negligible acoustic impedance ($\rho a$), the propagation velocity is related to the infinite fluid domain speed of sound and the structural properties via the following relation:

$$\frac{1}{\rho_{mix} a_{measured}^2} = \frac{1}{\rho_{mix} a_{mix}^2} + \sigma \quad \text{where} \quad \sigma \equiv \frac{2R}{Et} \qquad \text{Eq. 26}$$

where R=the pipe radius, t is the pipe wall thickness, $\rho_{mix}$ is the density of the mixture (or fluid), $a_{mix}$ is the actual speed of sound of the mixture, $a_{measured}$ is the measured speed of sound of the mixture contained in the pipe 12, and E is the Young's modulus for the pipe material. Eq. 26 holds primarily for frequencies where the wavelength of the acoustics is long (e.g., greater than about 2 to 1) compared to the diameter of the pipe and for frequencies which are low compared to the natural frequency of the breathing mode of the pipe. Eq. 26 also applies primarily to wavelengths which are long enough such that hoop stiffness dominates the radial deflections of the pipe.

For FIG. 18, the curve 352 (for 100% water) would be one of a family of curves for various different oil/water mixtures. For Eq. 26, the terms may be defined in terms of the density of each constituent, and the volumetric phase fraction as follows:

$$\frac{1}{\rho_{mix} a_{mix}^2} = \sum_{i=1}^{N} \frac{\phi_i}{\rho_i a_i^2} \quad \text{where:} \quad \rho_{mix} = \sum_{i=1}^{N} \phi_i \rho_i \quad \text{and} \quad \sum_{i=1}^{N} \phi_i = 1$$

where $\rho_i$ is the density of the i$^{th}$ constituent of a multi-component mixture, $a_i$ is the sound speed of the i$^{th}$ constituent of the mixture, $\phi_i$ is the volumetric phase fraction of the i$^{th}$ constituent of the mixture, and N is the number of components of the mixture. Knowing the pipe properties, the densities and the sound speed (in an infinite domain) of the individual constituents, and the measured sound speed of the mixture, Eq. 26 can be solved for $a_{mix}$. Thus, $a_{mix}$ can be determined for a compliant pipe. The calibration of the pipe can be derived from other equations or from a variety of other means, such as analytical, experimental, or computational.

For certain types of pressure sensors, e.g., pipe strain sensors, accelerometers, velocity sensors or displacement sensors, discussed hereinafter, it may be desirable for the pipe 12 to exhibit a certain amount of pipe compliance.

Alternatively, to minimize these error effects (and the need for the corresponding calibration) caused by pipe compliance, the axial test section 51 of the pipe 12 along where the sensors 14,16,18 are located may be made as rigid as possible. To achieve the desired rigidity, the thickness of the wall 53 of the test section 51 may be made to have a predetermined thickness, or the test section 51 may be made of a very rigid material, e.g., steel, titanium, Kevlar®, ceramic, or other material with a high modulus.

Regarding the second way, if the pipe 12 is compliant and acoustically coupled to fluids and materials outside the pipe 12 in the sensing region, such as the annulus fluid, casing, rock formations, etc., the acoustic properties of these fluids and materials outside the pipe 12 diameter may influence the measured speed of sound. Because the acoustic properties of such fluids and materials are variable and unknown, their affect on measured speed of sound cannot be robustly corrected by calibration (nor mapped to the propagation velocity in an infinite media in a predictable fashion).

Figure 20:
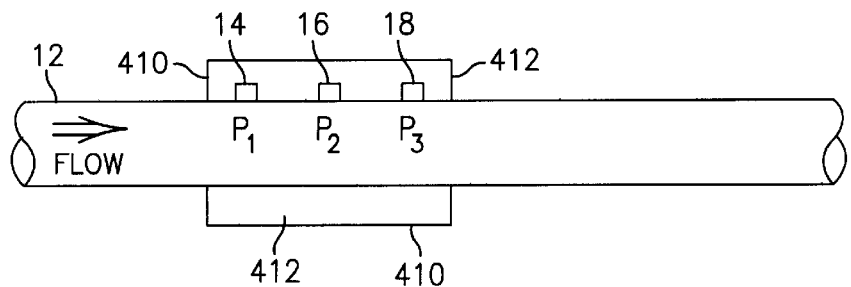
FIG. 20 is a side view of a pipe having an isolating sleeve around the sensing region of the pipe, in accordance with the present invention.

Referring to FIG. 20, to alleviate this effect, an outer isolation sleeve 410 (or sheath, shell, housing, or cover) which is attached to the outer surface of pipe 12 over where the pressure sensors 14,16,18 are located on the pipe 12. The sleeve 410 forms a closed chamber 412 between the pipe 12 and the sleeve 410. We have found that when the chamber 412 is filled with a gas such as air, the acoustic energy in the pipe is not acoustically coupled to fluids and materials outside the pipe 12 in the sensing region. As such, for a compliant pipe the speed of sound can be calibrated to the actual speed of sound in the fluid in the pipe 12 as discussed hereinbefore. The sleeve 410 is similar to that U.S. application Ser. No. 09/344,070, entitled "Measurement of Propagating Acoustic Waves in Compliant Pipes", filed Jun. 25, 1999, which is incorporated herein by reference.

Figure 19:
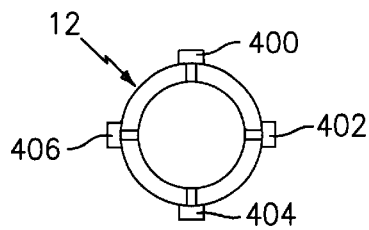
FIG. 19 is a cross-sectional view of a pipe, showing a plurality of sensors around the circumference of the pipe, in accordance with the present invention.

Referring to FIG. 19, instead of single point pressure sensors 14,16,18, at the axial locations x1,x2,x3 along the pipe 12, two or more pressure sensors, e.g., four sensors 400, 402, 404, 406, may be used around the circumference of the pipe 12 at each of the axial locations x1,x2,x3. The signals from the pressure sensors,400, 402, 404,406 around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 14,16,18 described herein may be any type of pressure sensor, capable of measuring the unsteady (or ac or dynamic ) pressures within a pipe, such as piezoelectric, optical, capacitive, resistive (e.g., Wheatstone bridge), accelerometers (or geophones), velocity measuring devices, displacement measuring devices, etc. If optical pressure sensors are used, the sensors 14,16,18 may be Bragg grating based pressure sensors, such as that described in U.S. patent application, Ser. No. 08/925,598, entitled "High Sensitivity Fiber Optic Pressure Sensor For Use In Harsh Environments", filed Sept. 8, 1997, now U.S. Pat. No. 6,016,702. Alternatively, the sensors 14,16,18 may be electrical or optical strain gages attached to or embedded in the outer or inner wall of the pipe which measure pipe wall strain, including microphones, hydrophones, or any other sensor capable of measuring the unsteady pressures within the pipe 12. In an embodiment of the present invention that utilizes fiber optics as the pressure sensors 14,16, 18, they may be connected individually or may be multiplexed along one or more optical fibers using wavelength division multiplexing (WDM), time division multiplexing (TDM), or any other optical multiplexing techniques (discussed more hereinafter).

Figure 21:
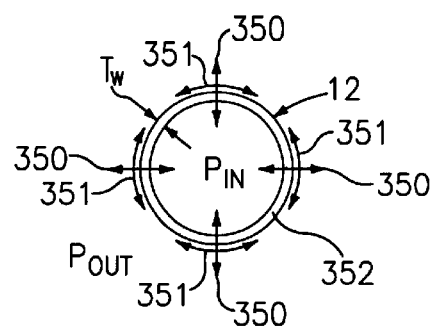
FIG. 21 is an end view of a pipe showing pressure inside and outside the pipe, in accordance with the present invention.

Referring to FIG. 21, if a strain gage is used as one or more of the pressure sensors 14,16,18, it may measure the unsteady (or dynamic or ac) pressure variations Pin inside the pipe 12 by measuring the elastic expansion and contraction, as represented by arrows 350, of the diameter (and thus the circumference as represented by arrows 351) of the pipe 12. In general, the strain gages would measure the pipe wall deflection in any direction in response to unsteady pressure signals inside the pipe 12. The elastic expansion and contraction of pipe 12 is measured at the location of the strain gage as the internal pressure $P_{in}$ changes, and thus measures the local strain (axial strain, hoop strain or off axis strain), caused by deflections in the directions indicated by arrows 351, on the pipe 12. The amount of change in the circumference is variously determined by the hoop strength of the pipe 12, the internal pressure $P_{in}$, the external pressure $P_{out}$ outside the pipe 12, the thickness $T_w$ of the pipe wall 352, and the rigidity or modulus of the pipe material. Thus, the thickness of the pipe wall 352 and the pipe material in the sensor sections 51 (FIG. 1) may be set based on the desired sensitivity of sensors 14,16,18 , and other factors and may be different from the wall thickness or material of the pipe 12 outside the sensing region 51.

Still with reference to FIG. 21 and FIG. 1, if an accelerometer is used as one or more of the pressure sensors 14,16,18, it may measure the unsteady (or dynamic or ac) pressure variations $P_{in}$ inside the pipe 12 by measuring the acceleration of the surface of pipe 12 in a radial direction, as represented by arrows 350. The acceleration of the surface of pipe 12 is measured at the location of the accelerometer as the internal pressure $P_{in}$ changes and thus measures the local elastic dynamic radial response of the wall 352 of the pipe. The magnitude of the acceleration is variously determined by the hoop strength of the pipe 12, the internal pressure $P_{in}$, the external pressure $P_{out}$ outside the pipe 12, the thickness $T_w$ of the pipe wall 352, and the rigidity or modulus of the pipe material. Thus, the thickness of the pipe wall 352 and the pipe material in the sensing section 51 (FIG. 1) may be set based on the desired sensitivity of sensors 14,16,18 and other factors and may be different from the wall thickness or material of the pipe 12 outside the sensing region 14. Alternatively, the pressure sensors 14,16, 18 may comprise a radial velocity or displacement measurement device capable of measuring the radial displacement characteristics of wall 352 of pipe 12 in response to pressure changes caused by unsteady pressure signals in the pipe 12. The accelerometer, velocity or displacement sensors may be similar to those described in commonly-owned copending U.S. Patent application, Ser. No. 09/344,069, entitled "Displacement Based Pressure Sensor Measuring Unsteady Pressure in a Pipe", filed Jun. 25, 1999 and incorporated herein by reference.

Figure 22:
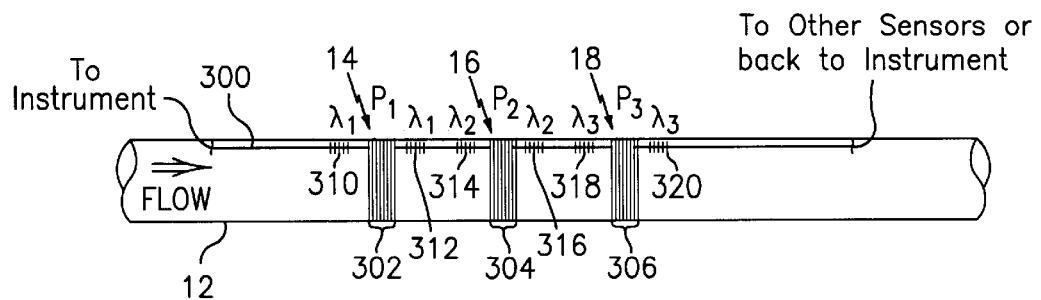
FIG. 22 is a side view of a pipe having optical fiber wrapped around the pipe at each unsteady pressure measurement location and a pair of Bragg gratings around each optical wrap, in accordance with the present invention.
Figure 23:
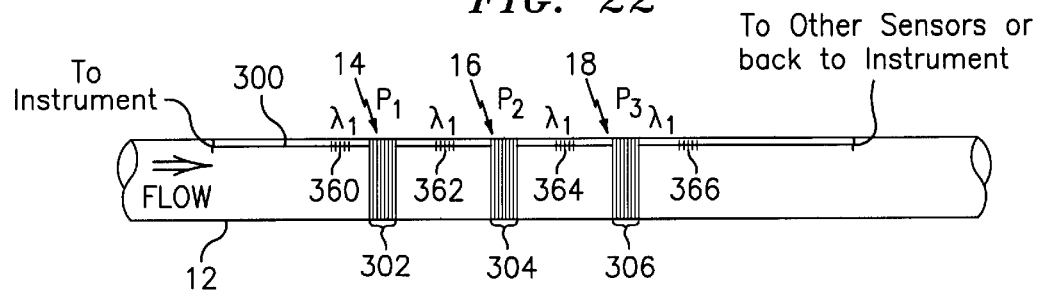
FIG. 23 is a side view of a pipe having optical fiber wrapped around the pipe at each unsteady pressure measurement location with a single Bragg grating between each pair of optical wraps, in accordance with the present invention.
Figure 24:
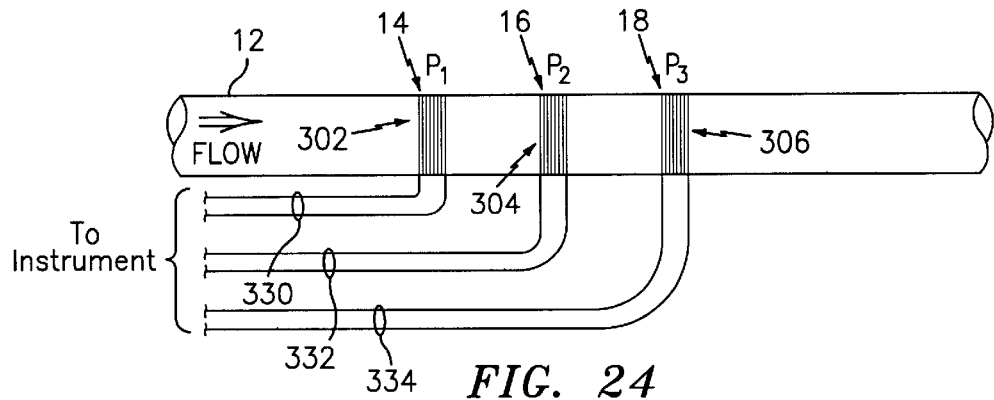
FIG. 24 is a side view of a pipe having optical fiber wrapped around the pipe at each unsteady pressure measurement location without Bragg gratings around each of the wraps, in accordance with the present invention.

Referring to FIGS. 22,23,24, if an optical strain gage is used, the ac pressure sensors 14,16,18 may be configured using an optical fiber 300 that is coiled or wrapped around and attached to the pipe 12 at each of the pressure sensor locations as indicated by the coils or wraps 302,304,306 for the pressures $P_1,P_2,P_3$, respectively. The fiber wraps 302, 304,306 are wrapped around the pipe 12 such that the length of each of the fiber wraps 302,304,306 changes with changes in the pipe hoop strain in response to unsteady pressure variations within the pipe 12 and thus internal pipe pressure is measured at the respective axial location. Such fiber length changes are measured using known optical measurement techniques as discussed hereinafter. Each of the wraps measure substantially the circumferentially averaged pressure within the pipe 12 at a corresponding axial location on the pipe 12. Also, the wraps provide axially averaged pressure over the axial length of a given wrap. While the structure of the pipe 12 provides some spatial filtering of short wavelength disturbances, we have found that the basic principle of operation of the invention remains substantially the same as that for the point sensors described hereinbefore.

Referring to FIG. 22, for embodiments of the present invention where the wraps 302,304,306 are connected in series, pairs of Bragg gratings (310,312),(314,316), (318, 320) may be located along the fiber 300 at opposite ends of each of the wraps 302,304,306, respectively. The grating pairs are used to multiplex the pressure signals $P_1,P_2,P_3$ to identify the individual wraps from optical return signals. The first pair of gratings 310,312 around the wrap 302 may have a common reflection wavelength $\lambda_1$, and the second pair of gratings 314,316 around the wrap 304 may have a common reflection wavelength $\lambda_2$, but different from that of the first pair of gratings 310,312. Similarly, the third pair of gratings 318,320 around the wrap 306 have a common reflection wavelength $\lambda_3$, which is different from $\lambda_1,\lambda_2$.

Referring to FIG. 23, instead of having a different pair of reflection wavelengths associated with each wrap, a series of Bragg gratings 360, 362, 364, 366 with only one grating between each of the wraps 302, 304, 306 may be used each having a common reflection wavlength $\lambda_1$.

Referring to FIGS. 22 and 23 the wraps 302, 304, 306 with the gratings 310, 312, 314, 316, 318, 320 (FIG. 22) or with the gratings 360, 362, 364, 366 (FIG. 23) may be configured in numerous known ways to precisely measure the fiber length or change in fiber length, such as an interferometric, Fabry Perot, time-of-flight, or other known arrangements. An example of a Fabry Perot technique is described in U.S. Pat. No. 4,950,883 "Fiber Optic Sensor Arrangement Having Reflective Gratings Responsive to Particular Wavelengths", to Glenn. One example of time-of-flight (or Time-Division-Multiplexing; TDM) would be where an optical pulse having a wavelength is launched down the fiber 300 and a series of optical pulses are reflected back along the fiber 300. The length of each wrap can then be determined by the time delay between each return pulse.

Alternatively, a portion or all of the fiber between the gratings (or including the gratings, or the entire fiber, if desired) may be doped with a rare earth dopant (such as erbium) to create a tunable fiber laser, such as is described in U.S. Pat. No. 5,317,576, "Continuously Tunable Single Mode Rare-Earth Doped Laser Arrangement", to Ball et al or U.S. Pat. No. 5,513,913, "Active Multipoint Fiber Laser Sensor", to Ball et al, or U.S. Pat. No. 5,564,832, "Birefringent Active Fiber Laser Sensor", to Ball et al, which are incorporated herein by reference.

While the gratings 310, 312, 314, 316, 318, 320 are shown oriented axially with respect to pipe 12, in FIGS. 22,23, they may be oriented along the pipe 12 axially, circumferentially, or in any other orientations. Depending on the orientation, the grating may measure deformations in the pipe wall 352 with varying levels of sensitivity. If the grating reflection wavelength varies with internal pressure changes, such variation may be desired for certain configurations (e.g., fiber lasers) or may be compensated for in the optical instrumentation for other configurations, e.g., by allowing for a predetermined range in reflection wavelength shift for each pair of gratings. Alternatively, instead of each of the wraps being connected in series, they may be connected in parallel, e.g., by using optical couplers (not shown) prior to each of the wraps, each coupled to the common fiber 300.

Referring to FIG. 24, alternatively, the sensors 14, 16, 18 may also be formed as a purely interferometric sensor by wrapping the pipe 12 with the wraps 302, 304, 306 without using Bragg gratings where separate fibers 330,332,334 may be fed to the separate wraps 302,304,306, respectively. In this particular embodiment, known interferometric techniques may be used to determine the length or change in length of the fiber 10 around the pipe 12 due to pressure changes, such as Mach Zehnder or Michaelson Interferometric techniques, such as that described in U.S. Pat. No. 5,218,197, entitled "Method and Apparatus for the Non-invasive Measurement of Pressure Inside Pipes Using a Fiber Optic Interferometer Sensor" to Carroll. The inteferometric wraps may be multiplexed such as is described in Dandridge, et al, "Fiber Optic Sensors for Navy Applications", IEEE, February 1991, or Dandridge, et al, "Multiplexed Interoferometric Fiber Sensor Arrays", SPIE, Vol. 1586, 1991, pp176–183. Other techniques to determine the change in fiber length may be used. Also, reference optical coils (not shown) may be used for certain interferometric approaches and may also be located on or around the pipe 12 but may be designed to be insensitive to pressure variations.

Figure 25:
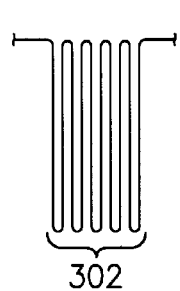
FIG. 25 is an alternative geometry of an optical wrap of FIGS. 21, 22, of a radiator tube geometry, in accordance with the present invention.
Figure 26:
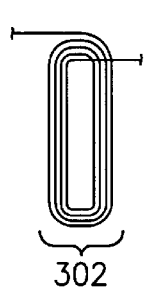
FIG. 26 is an alternative geometry of an optical wrap of FIGS. 21, 22, of a race track geometry, in accordance with the present invention.

Referring to FIGS. 25 and 26, instead of the wraps 302, 304, 306 being optical fiber coils wrapped completely around the pipe 12, the wraps 302, 304, 306 may have alternative geometries, such as a "radiator coil" geometry (FIG. 25) or a "race-track" geometry (FIG. 26), which are shown in a side view as if the pipe 12 is cut axially and laid flat. In this particular embodiment, the wraps 302–206 are not necessarily wrapped 360 degrees around the pipe, but may be disposed over a predetermined portion of the circumference of the pipe 12, and have a length long enough to optically detect the changes to the pipe circumference. Other geometries for the wraps may be used if desired. Also, for any geometry of the wraps described herein, more than one layer of fiber may be used depending on the overall fiber length desired. The desired axial length of any particular wrap is set depending on the characteristics of the ac pressure desired to be measured, for example the axial length of the pressure disturbance caused by a vortex to be measured.

Figure 27:
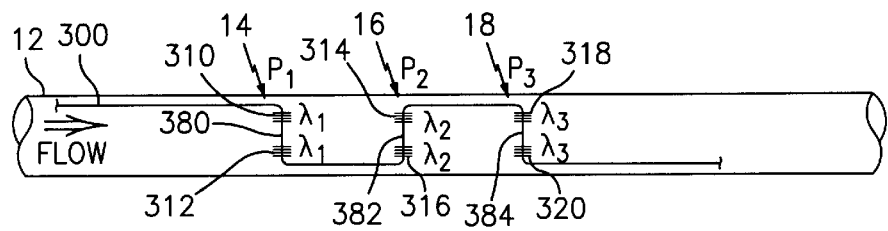
FIG. 27 is a side view of a pipe having a pair of gratings at each axial sensing location, in accordance with the present invention.
Figure 28:
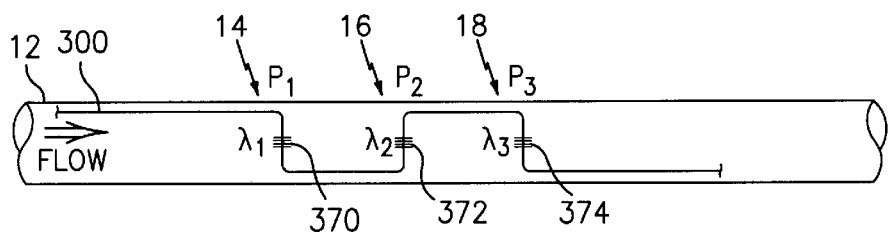
FIG. 28 is a side view of a pipe having a single grating at each axial sensing location, in accordance with the present invention.

Referring to FIGS. 27 and 28, embodiments of the present invention include configurations wherein instead of using the wraps 302, 304, 306, the fiber 300 may have shorter sections that are disposed around at least a portion of the circumference of the pipe 12 that can optically detect changes to the pipe circumference. It is further within the scope of the present invention that sensors may comprise an optical fiber 300 disposed in a helical pattern (not shown) about pipe 12. As discussed herein above, the orientation of the strain sensing element will vary the sensitivity to deflections in pipe wall 352 deformations caused by unsteady pressure signals in the pipe 12.

Referring to FIG. 27, in particular, the pairs of Bragg gratings (310,312), (314,316), (318,320) are located along the fiber 300 with sections 380, 382, 384 of the fiber 300 between each of the grating pairs, respectively. In that case, known Fabry Perot, interferometric, time-of-flight or fiber laser sensing techniques may be used to measure the strain in the pipe, in a manner similar to that described in the aforementioned references.

Referring to FIG. 28, alternatively, individual gratings 370, 372, 374 may be disposed on the pipe and used to sense the unsteady variations in strain in the pipe 12 (and thus the unsteady pressure within the pipe) at the sensing locations. When a single grating is used per sensor, the grating reflection wavelength shift will be indicative of changes in pipe diameter and thus pressure.

Any other technique or configuration for an optical strain gage may be used. The type of optical strain gage technique and optical signal analysis approach is not critical to the present invention, and the scope of the invention is not intended to be limited to any particular technique or approach.

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 12. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe 12 if desired.

Figure 29:
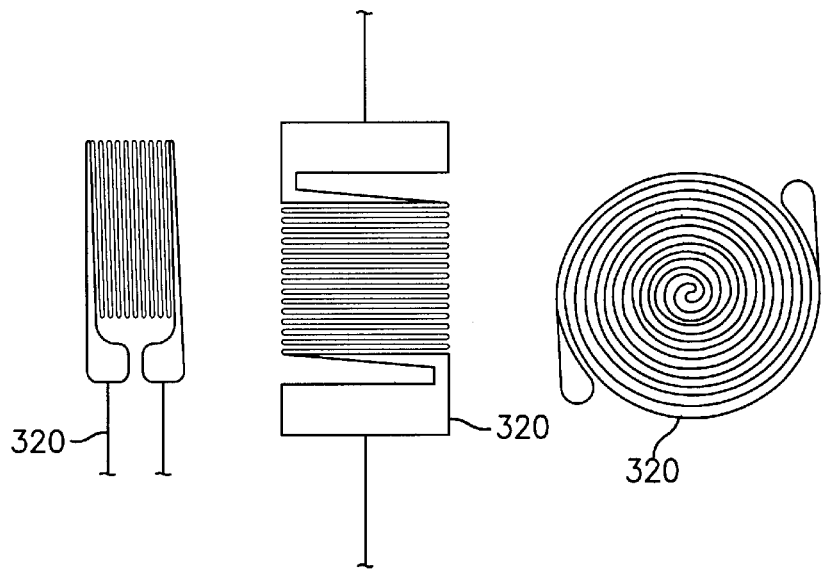
FIG. 29 is a top view of three alternative strain gauges, in accordance with the present invention.
Figure 30:
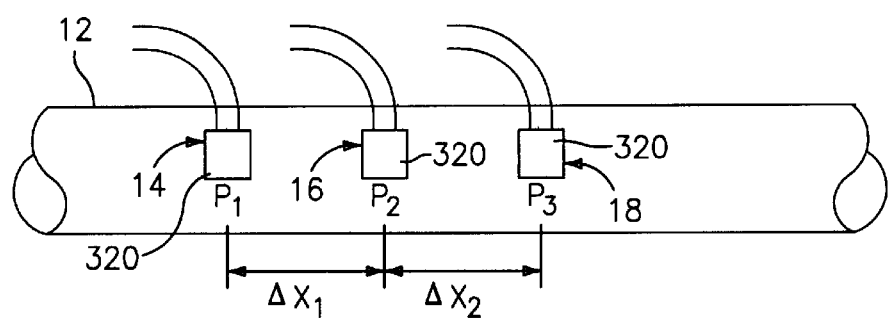
FIG. 30 is a side view of a pipe having three axially spaced strain gauges attached thereto, in accordance with the present invention.

Referring to FIGS. 29,30, it is also within the scope of the present invention that any other strain sensing technique may be used to measure the variations in strain in the pipe, such as highly sensitive piezoelectric, electronic or electric, strain gages attached to or embedded in the pipe 12. Referring to FIG. 29, different known configurations of highly sensitive piezoelectric strain gages are shown and may comprise foil type gages. Referring to FIG. 30, an embodiment of the present invention is shown wherein pressure sensors 14, 16, 18 comprise strain gages 320. In this particular embodiment strain gages 320 are disposed about a predetermined portion of the circumference of pipe 12. The axial placement of and separation distance $\Delta X_1$, $\Delta X_2$ between the pressure sensors 14, 16, 18 are determined as described herein above.

Figure 31:
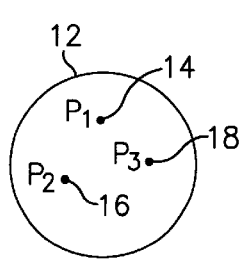
FIG. 31 is an end view of a pipe having three unsteady pressure sensors spaced apart from each other within the pipe, in accordance with the present invention.
Figure 32:
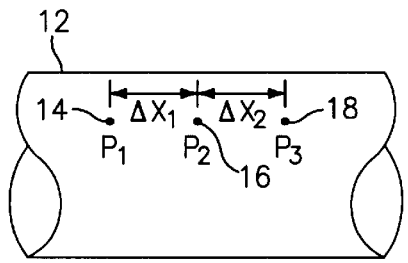
FIG. 32 is a side view of a pipe having three unsteady pressure sensors spaced axially within the pipe, in accordance with the present invention.
Figure 33:
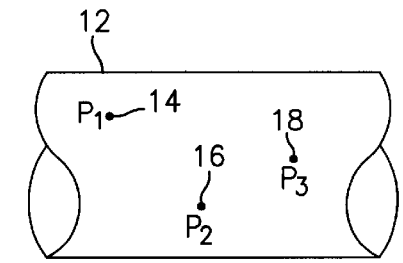
FIG. 33 is a side view of a pipe having three unsteady pressure sensors axially and radially spaced within the pipe, in accordance with the present invention.

Referring to FIGS. 31–33, instead of measuring the unsteady pressures $P_1$–$P_3$ on the exterior of the pipe 12, the invention will also work when the unsteady pressures are measured inside the pipe 12. In particular, the pressure sensors 14, 16, 18 that measure the pressures $P_1,P_2,P_3$ may be located anywhere within the pipe 12 and any technique may be used to measure the unsteady pressures inside the pipe 12.

Figure 34:
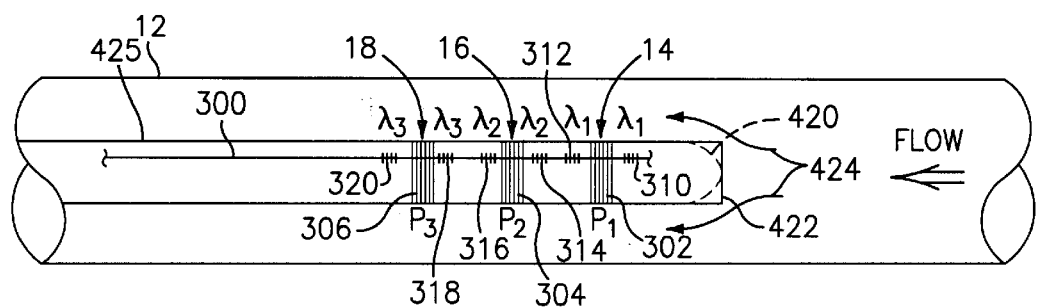
FIG. 34 is a side view of a pipe having an inner tube with axially distributed optical fiber wraps for unsteady pressure sensors, in accordance with the present invention.
Figure 35:
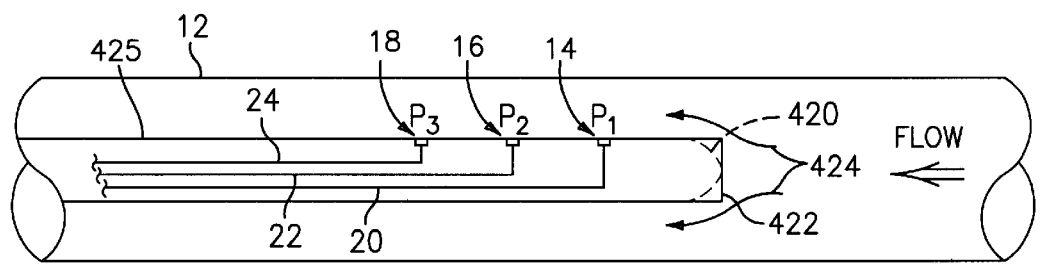
FIG. 35 is a side view of a pipe having an inner tube with axially distributed unsteady pressure sensors located along the tube, in accordance with the present invention.
Figure 36:
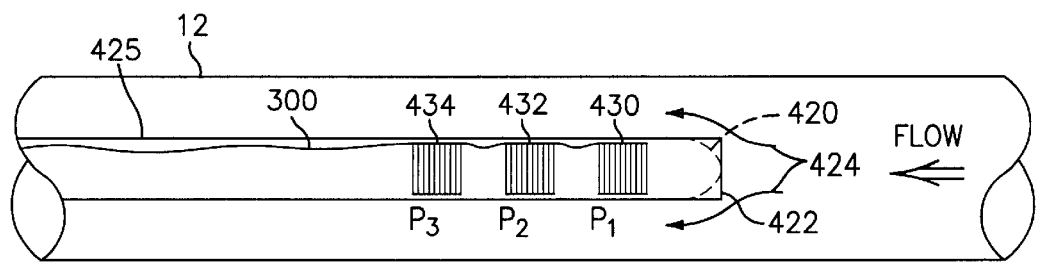
FIG. 36 is a side view of a pipe having an inner tube with three axially distributed hydrophones located within the tube, in accordance with the present invention.

Referring to FIGS. 34–36, the invention may also measure the speed of sound of a mixture flowing outside a pipe or tube 425. In that case, the tube 425 may be placed within the pipe 12 and the pressures $P_1$–$P_3$ measured at the outside of the tube 425. Any technique may be used to measure the unsteady pressures $P_1$–$P_3$ outside the tube 425. Referring to FIG. 34, for example, the tube 425 may have the optical wraps 302, 304, 306 wrapped around the tube 425 at each sensing location. Alternatively, any of the strain measurement or displacement, velocity or accelerometer sensors or techniques described herein may be used on the tube 425. Referring to FIG. 35, alternatively, the pressures $P_1$–$P_3$ may be measured using direct pressure measurement sensors or techniques described herein. Any other type of unsteady pressure sensors 14, 16, 18 may be used to measure the unsteady pressures within the pipe 12.

Alternatively, referring to FIG. 36, hydrophones 430, 432, 434 may be used to sense the unsteady pressures within the pipe 12. In that case, the hydrophones 430, 432, 434 may be located in the tube 425 for ease of deployment or for other reasons. The hydrophones 430, 432, 434 may be fiber optic, electronic, piezoelectric or other types of hydrophones. If fiber optic hydrophones are used, the hydrophones 430, 432, 434 may be connected in series or parallel along the common optical fiber 300.

The tube 425 may be made of any material that allows the unsteady pressure sensors to measure the pressures $P_1$–$P_3$ and may be hollow, solid, or gas filled or fluid filled. One example of a dynamic pressure sensor is described in co-pending commonly-owned U.S. Patent application, Ser. No. 09/326,097 entitled "Mandrel Wound Fiber Optic Pressure Sensor", filed Jun. 4, 1999. Also, the end 422 of the tube 425 is closed and thus the flow path would be around the end 422 as indicated by lines 424. For oil and gas well applications, the tube 425 may be coiled tubing or equivalent deployment tool having the pressure sensors 14, 16, 18 for sensing $P_1$–$P_3$ inside the tubing 425. Alternatively the tube 425 may also include a bluff or rounded shaped end as indicated by dashed line 420.

Figure 17:
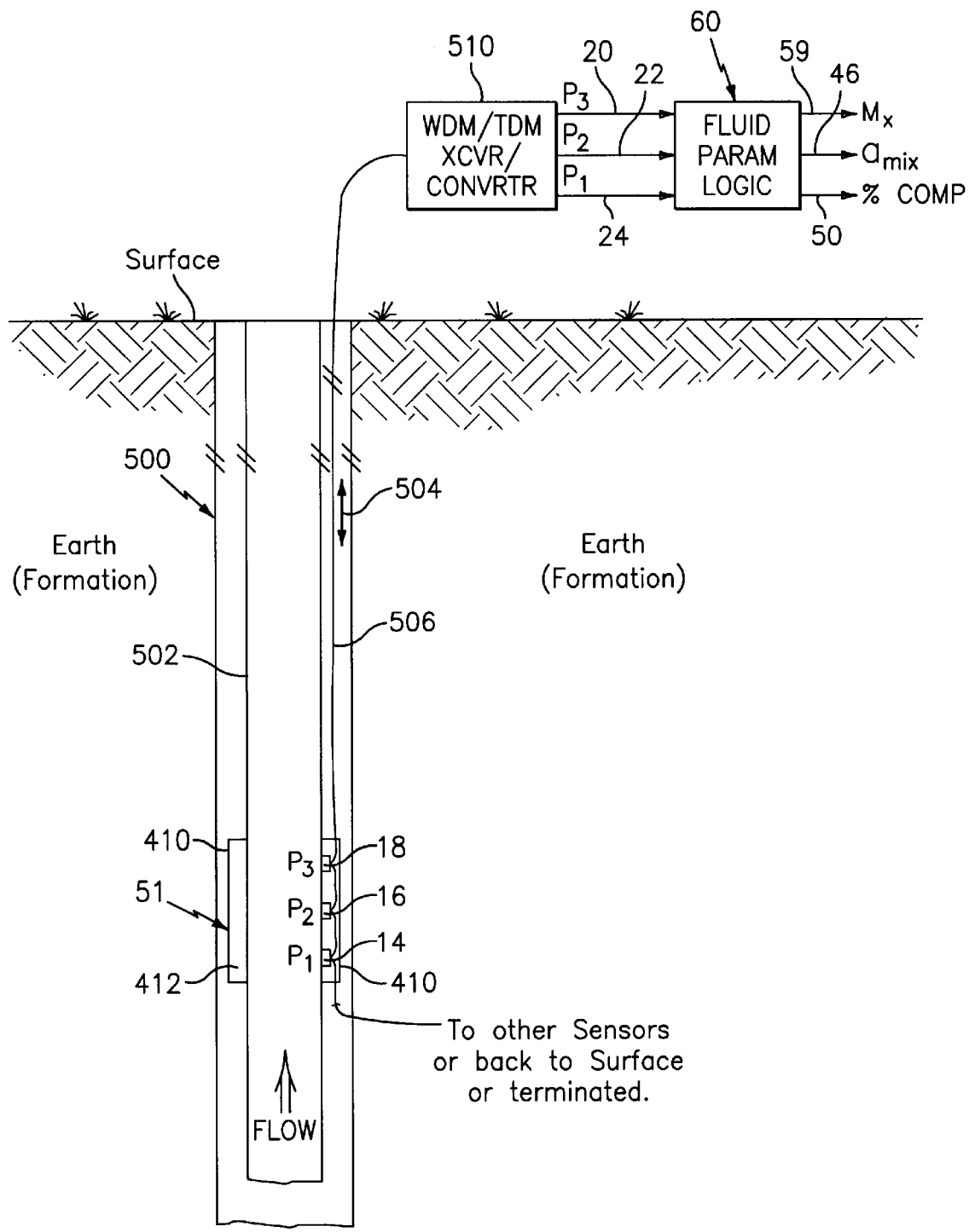
FIG. 17 is a schematic block diagram of a fluid parameter measurement system, in an oil or gas well application, using fiber optic sensors, in accordance with the present invention.

Referring to FIG. 17, there is shown an embodiment of the present invention in an oil or gas well application, the sensing section 51 may be connected to or part of production tubing 502 (analogous to the pipe 12 in the test section 51) within a well 500. The isolation sleeve 410 may be located over the sensors 14, 16, 18 as discussed hereinbefore and attached to the pipe 502 at the axial ends to protect the sensors 14, 16, 18 (or fibers) from damage during deployment, use, or retrieval, and/or to help isolate the sensors from acoustic external pressure effects that may exist outside the pipe 502, and/or to help isolate ac pressures in the pipe 502 from ac pressures outside the pipe 502. The sensors 14, 16, 18 are connected to a cable 506 which may comprise the optical fiber 300 (FIGS. 22,23,27,28) and is connected to a transceiver/converter 510 located outside the well 500.

When optical sensors are used, the transceiver/converter 510 may be used to receive and transmit optical signals 504 to the sensors 14, 16, 18 and provides output signals indicative of the pressure $P_1$–$P_3$ at the sensors 14, 16, 18 on the lines, 20, 22, 24, respectively. Also, the transceiver/converter 510 may be part of the Fluid Parameter Logic 60. The transceiver/converter 510 may be any device that performs the corresponding functions described herein. In particular, the transceiver/converter 510 together with the optical sensors described hereinbefore may use any type of optical grating-based measurement technique, e.g., scanning interferometric, scanning Fabry Perot, acousto-optic-tuned filter (AOTF), optical filter, time-of-flight, and may use WDM and/or TDM, etc., having sufficient sensitivity to measure the ac pressures within the pipe, such as that described in one or more of the following references: A. Kersey et al., "Multiplexed fiber Bragg grating strain-sensor system with a Fabry-Perot wavelength filter", Opt. Letters, Vol 18, No. 16, August 1993, U.S. Pat. No. 5,493,390, issued Feb. 20, 1996 to Mauro Verasi, et al., U.S. Pat. No. 5,317, 576, issued May 31, 1994, to Ball et al., U.S. Pat. No. 5,564,832, issued Oct. 15, 1996 to Ball et al., U.S. Pat. No. 5,513,913, issued May 7, 1996, to Ball et al., U.S. Pat. No. 5,426,297, issued Jun. 20, 1995, to Dunphy et al., U.S. Pat. No. 5,401,956, issued Mar. 28, 1995 to Dunphy et al., U.S. Pat. No. 4,950,883, issued Aug. 21, 1990 to Glenn, and U.S. Pat. No. 4,996,419, issued Feb. 26, 1991 to Morey all of which are incorporated by reference. Also, the pressure sensors described herein may operate using one or more of the techniques described in the aforementioned references.

A plurality of the sensors 10 of the present invention may be connected to a common cable and multiplexed together using any known multiplexing technique.

It should be understood that the present invention can be used to measure fluid volume fractions of a mixture of any number of fluids in which the speed of sound of the mixture $a_{mix}$ is related to (or is substantially determined by), the volume fractions of two constituents of the mixture, e.g., oil/water, oil/gas, water/gas. The present invention can be used to measure the speed of sound of any mixture and can then be used in combination with other known quantities to derive phase content of mixtures with multiple (more than two) constituents.

Further, the present invention can be used to measure any parameter (or characteristic) of any mixture of one or more fluids in which such parameter is related to the speed of sound of the mixture $a_{mix}$, e.g., fluid fraction, temperature, salinity, mineral content, sand particles, slugs, pipe properties, etc. or any other parameter of the mixture that is related to the speed of sound of the mixture. Accordingly, the logic 48 (FIG. 1) may convert $a_{mix}$ to such parameter(s).

Further, the invention will work independent of the direction of the flow or the amount of flow of the fluid(s) in the pipe, and whether or not there is flow in the pipe. Also, independent of the location, characteristics and/or direction (s) of propagation of the source of the acoustic pressures. Also, instead of a pipe, any conduit or duct for carrying a fluid may be used if desired.

Also, the signals on the lines 20,22,24 (FIG. 1) may be time signals $H_1(t), H_2(t), H_3(t)$, where Hn(t) has the pressure signal Pn(t) as a component thereof, such that $FFT[H_1(t)] = G(\omega)P_1(\omega)$, $FFT[H_2(t)] = G(\omega)P_2(\omega)$, and the ratio $H_2(\omega)/H_1(\omega) = G(\omega)P_2(\omega)/G(\omega)P_1(\omega) = P_2(\omega)/P_1(\omega)$, where $G(\omega)$ is a parameter which is inherent to each pressure signal and may vary with temperature, pressure, or time, such as calibration characteristics, e.g., drift, linearity, etc.

Also, Instead of calculating the ratios $P_{12}$ and $P_{13}$, equations similar to Eqs. 9,10 may be derived by obtaining the ratios of any other two pairs of pressures, provided the system of equations Eq. 5–7 are solved for B/A or A/B and the ratio of two pairs of pressures. Also, the equations shown herein may be manipulated differently to achieve the same result as that described herein.

Still further, if, for a given application, the relationship between A and B (i.e., the relationship between the right and left travelling waves, or the reflection coefficient R) is known, or the value of A or B is known, or the value of A or B is zero, only two of the equations 5–7 are needed to determine the speed of sound. In that case, the speed of sound $a_{mix}$ can be measured using only two axially-spaced acoustic pressure sensors along the pipe.

Further, while the invention has been described as using a frequency domain approach, a time domain approach may be used instead. In particular, the Eqs. 5,6,7 may be written in the form of Eq. 1 in the time-domain giving time domain equations $P_1(x_1,t), P_2(x_2,t), P_3(x_3,t)$, and solved for the speed of sound $a_{mix}$ and eliminating the coefficients A,B using known time domain analytical and signal processing techniques (e.g., convolution).

Referring to FIGS. 37–40, it should be understood that although the invention has been described hereinbefore as using the one dimensional acoustic wave equation evaluated at a series of different axial locations to determine the speed of sound, any known technique to determine the speed at which sound propagates along a spatial array of acoustic pressure measurements where the direction of the source(s) is (are) known may be used to determine the speed of sound in the mixture. The term acoustic signals as used herein, as is known, refers to substantially stochastic, time stationary signals, which have average (or RMS) statistical properties that do not significantly vary over a predetermined period of time (i.e., non-transient ac signals).

For example, the procedure for determining the one dimensional speed of sound $a_{mix}$ within a fluid contained in a pipe using an array of unsteady pressure measurements is similar to a problem encountered in underwater acoustics (e.g., SONAR or Sound Navigation Ranging). In underwater acoustics, axial arrays of sensors are deployed to determine the bearing (or direction) of underwater noise sources. The process is referred to as "beam forming". In free space, i.e., in an unbounded media, such as the ocean, the speed at which a sound wave propagates along an axial array is dependent on both (1) the free-space speed of sound and (2) the incident angle of the sound wave on the axial array.

Figure 37:
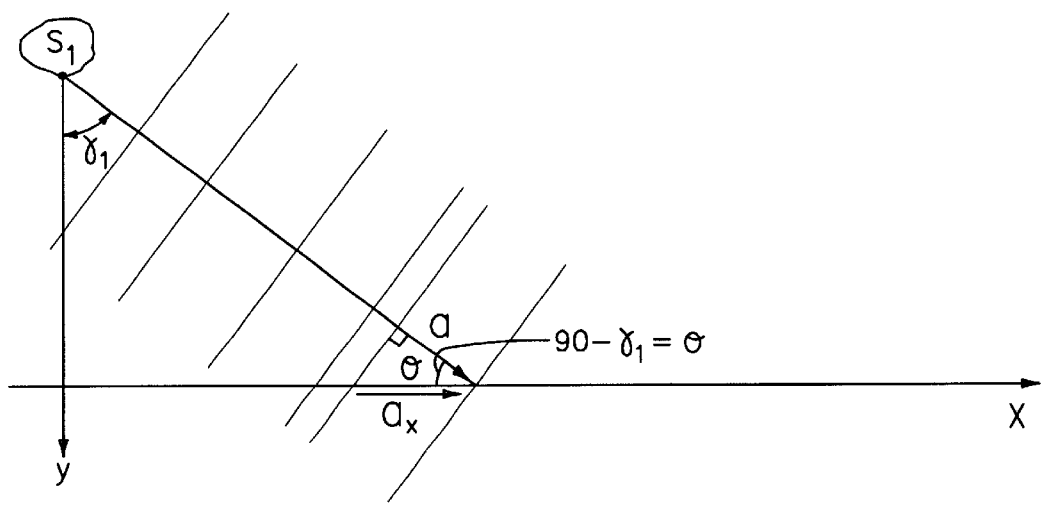
FIG. 37 is a diagram showing the propagation of acoustic waves from a single source in two dimensional space onto a spatial array, in accordance with the present invention.

Referring to FIG. 37, the apparent sound speed $a_x$ at which the wave propagates along the array is related to the angle or bearing ($\theta=90-\gamma$) of the source S1 and the sound speed a in the media. For a SONAR application, as is known, the speed of sound is known and the apparent sound speed $a_x$ is measured, which allows the bearing to be determined by the relation: $\theta = \cos^{-1}(a/a_x)$.

Conversely, referring to FIG. 38, we have found that in a pipe 12 where the angle or bearing on the array of the incident sound is known, i.e., $\theta=0$ deg, the speed of sound a of the fluid in the pipe 12 can be determined as follows.

Figure 39:
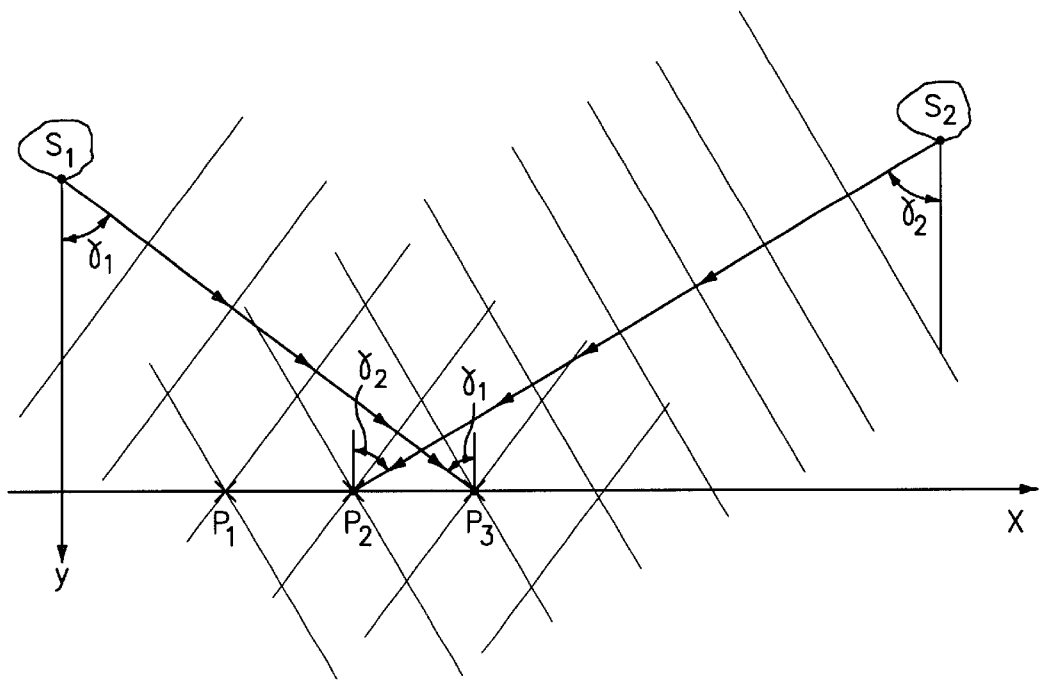
FIG. 39 is a diagram showing the propagation of acoustic waves from two sources in two dimensional space onto a spatial array, in accordance with the present invention.

In particular, referring to FIG. 39, for a single distant source in two dimensional (2D) space, the pressure wave can be written as follows (such as is generally described in A. Dowling and J. Williams, "Sound and Sources of Sound", Ch 4, pp 79–81):

$$P(x,y,t) = Ae^{i\omega(t - x \sin \gamma_1/a - y\cos \gamma_1/a)} \qquad \text{Eq. 27}$$

Pressure as seen on the array at y=0 is:

$$P(x,y=0,t) = Ae^{i\omega(t - x \sin \gamma_1/a)} \qquad \text{Eq. 28}$$

$$P(x,t) = Ae^{-ik_{xr}x}e^{i\omega t} \qquad \text{Eq. 29}$$

where:

$$k_{xr} = (\sin \gamma_1)\frac{\omega}{a}.$$

A similar analysis may be done for a left travelling wave along the array from the source S2 as:

$$P(x,t) = Be^{+ik_{xl}x}e^{i\omega t} \qquad \text{Eq. 30}$$

where:

$$k_{xl} = (\sin \gamma_2)\frac{\omega}{a}.$$

For the situation where the sound is propagating along a pipe, then $\gamma_1 = \gamma_2 = 90$ deg. and where a=amix which is the speed of sound of the fluid mixture in the pipe, then:

$$k_{xr} = k_{xl} = \frac{\omega}{a_{mix}} \qquad \text{Eq. 31}$$

Figure 38:
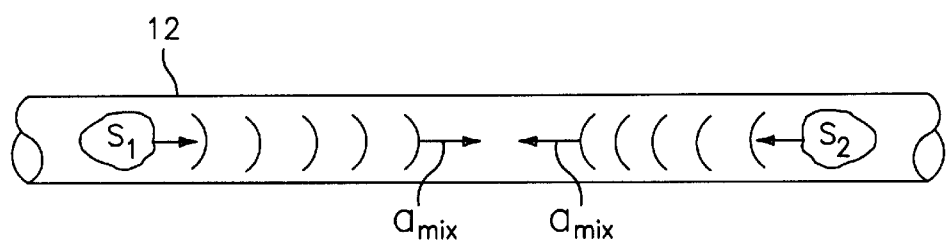
FIG. 38 is a side view of a pipe having left and right travelling acoustic waves propagating along the pipe, in accordance with the present invention.

Thus, referring to FIG. 38, for a left and right travelling acoustic waves travelling in the pipe 12, the pressure equation becomes:

$$P(x,t) = Ae^{-ik_{xr}x}e^{i\omega t} + Be^{+ik_{xl}x}e^{i\omega t} \qquad \text{Eq. 32}$$

which is the same as Eq. 1, and which may be used to determine the speed of sound by using the sensors described herein and solving the associated equations Eq. 5–7 shown hereinbefore. The same result may also be shown from sources originating in three dimensional space using cylindrical or other coordinate systems.

The data from the array of sensors may be processed in any domain, including the frequency/spatial domain (such as Eq. 4), the temporal/spatial domain (such as Eq. 1), the temporal/wave-number domain or the wave-number/frequency (k–ω) domain. As such, any known array processing technique in any of these or other related domains may be used if desired.

For example, Eq. 5 can be represented in the k–ω domain by taking the spatial Fourier transform of Eq. 5, resulting in the following k–ω representation:

$$P(k, \omega) = \frac{1}{2\pi} \int_{-\infty}^{+\infty} P(x, \omega) e^{ikx} dx \quad \text{Eq. 33}$$

$$= A(\omega)\delta\left(k - \frac{\omega}{a}\right) + B(\omega)\delta\left(k + \frac{\omega}{a}\right)$$

where k is the wave number and δ is the Dirac delta function, which shows a spatial/temporal mapping of the acoustic field in the k–ω plane.

Alternatively, instead of using the three equations Eq. 5–7, any technique known in the art for using a spatial (or phased) array of sensors to determine the direction of an acoustic source in three dimensional sound field with a known speed of sound (e.g., spatial array processing for SONAR arrays, RADAR (RAdio Detecting And Ranging) arrays or other arrays, beam forming, or other signal processing techniques), may be used to solve for the sound speed knowing the direction of travel of the acoustic waves, i.e., axially along the pipe. Some of such known techniques are described in the following references, which are incorporated herein by reference: H. Krim, M. Viberg, "Two Decades of Array Signal Processing Research—The Parametric Approach", IEEE Signal Processing Magazine, pp 67–94, R. Nielson, "Sonar Signal Processing", Ch. 2, pp51–59.

Figure 40:
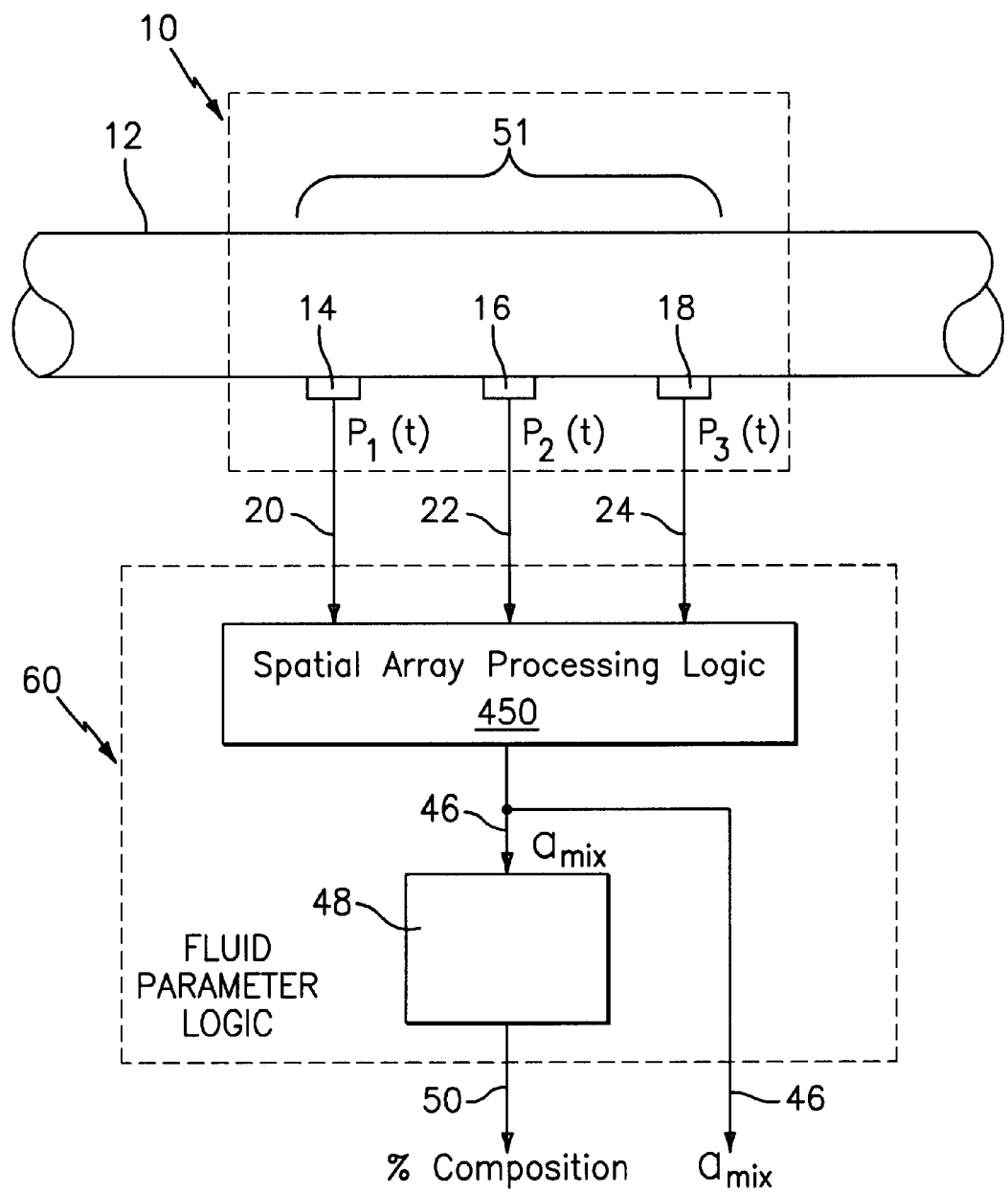
FIG. 40 is a schematic block diagram of an alternative embodiment of a fluid parameter measurement system, in accordance with the present invention.

Referring to FIG. 40, accordingly, the fluid parameter logic 60 may comprise spatial array processing logic 450 which receives the spatial array of acoustic pressure signals $P_1(t)$, $P_2(t)$, $P_3(t)$ and performs the spatial array processing described herein to determine the speed of sound $a_{mix}$ on the line 46.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring at least one parameter of a mixture of at least one fluid in a pipe, comprising:

a spatial array of at least two pressure sensors, disposed at different axial locations along the pipe, and each measuring an acoustic pressure within the pipe at a corresponding axial location, at least one of said pressure sensors measures a circumference-averaged pressure at said axial location of said sensor, each of said sensors providing an acoustic pressure signal indicative of the acoustic pressure within the pipe at said axial location of a corresponding one of said sensors; and a signal processor, responsive to said pressure signals, which provides a signal indicative of a speed of sound of the mixture in the pipe.

2. The apparatus of claim 1 wherein said signal processor comprises logic which calculates a speed at which sound propagates along said spatial array.

3. The apparatus of claim 1 wherein said signal processor comprises logic which calculates a frequency based signal for each of said acoustic pressure signals.

4. The apparatus of claim 2 wherein said acoustic pressure signals each comprise a frequency based signal and wherein said signal processor comprises logic which calculates a ratio of two of said frequency based signals.

5. The apparatus of claim 1 comprising at least three of said sensors.

6. The apparatus of claim 1 comprising three of said sensors and wherein said signal processor comprises logic which simultaneously solves the following equations for said speed of sound:

$$P(x_1,t) = (Ae^{-ik_r x_1} + Be^{+ik_l x_1})e^{i\omega t}$$
$$P(x_2,t) = (Ae^{-ik_r x_2} + Be^{+ik_l x_2})e^{i\omega t}$$
$$P(x_3,t) = (Ae^{-ik_r x_3} + Be^{+ik_l x_3})e^{i\omega y}$$

where A,B are amplitudes of the frequency based signals, x is the axial location of the pressure sensor along the pipe, t is time, ω is frequency and $k_r, k_l$ are wave numbers.

7. The apparatus of claim 1 wherein said signal processor calculates said speed of sound of said mixture using the following relation:

$$\frac{e^{-ik_r x_1} + Re^{ik_l x_1}}{e^{-ik_r x_3} + Re^{ik_l x_3}} - \left[\frac{P_1(\omega)}{P_3(\omega)}\right] = 0 \quad \text{where}$$

$$R \equiv \frac{B}{A} = \frac{e^{-ik_r x_1} - \left[\frac{P_1(\omega)}{P_2(\omega)}\right]e^{-ik_r x_2}}{\left[\frac{P_1(\omega)}{P_2(\omega)}\right]e^{ik_l x_2} - e^{ik_l x_1}} \quad \text{where}$$

$$k_r \equiv \left(\frac{\omega}{a_{mix}}\right)\frac{1}{1+M_x} \quad \text{and} \quad k_l \equiv \left(\frac{\omega}{a_{mix}}\right)\frac{1}{1-M_x}$$

where $a_{mix}$ is the speed of sound of the mixture in the pipe, ω is frequency (in rad/sec), and $M_x$ is the axial Mach number of the flow of the mixture within the pipe, where:

$$M_x \equiv \frac{V_{mix}}{a_{mix}}$$

and where Vmix is the axial velocity of the mixture, and where $P_1(\omega), P_2(\omega), P_3(\omega)$ are said frequency based signals for each of said acoustic pressure signals.

8. The apparatus of claim 1 wherein said sensors are equally spaced, a Mach number of the mixture is small compared to one, and said signal processor calculates the speed of sound of the mixture using the following relation:

$$a_{mix} = \frac{\omega}{\left[\frac{1}{\Delta x}\right] i \log\left[\frac{P_{12} + P_{13}P_{12} + (P_{12}^2 + 2P_{13}P_{12}^2 + P_{13}^2 P_{12}^2 - 4P_{13}^2)^{1/2}}{2P_{13}}\right]}$$

where $P_{12} = P_1(\omega)/P_2(\omega), P_{13} = P_1(\omega)/P_3(\omega)$, i is the square root of −1, Δx is the axial spacing between sensors, where $a_{mix}$ is the speed of sound of the mixture in the pipe, ω is frequency (in rad/sec), and where $P_1(\omega), P_2(), P_3(\omega)$ are said frequency based signals for each of said acoustic pressure signals.

9. The apparatus of claim 1 wherein said sensors are equally axially spaced, a Mach number of the mixture is small compared to one, and said signal processor calculates the speed of sound of the mixture using the following relation:

$$\frac{P_1(\omega) + P_3(\omega)}{P_2(\omega)} = 2\cos\left(\frac{\omega \Delta x}{a_{mix}}\right)$$

where $a_{mix}$ is the speed of sound of the mixture in the pipe, $\omega$ is frequency (in rad/sec), $\Delta x$ is the axial spacing between said sensors, and where $P_1(\omega), P_2(\omega), P_3(\omega)$ are said frequency based signals for each of said acoustic pressures signals.

10. The apparatus of claim 1 wherein the signal processor comprises logic which calculates a fluid composition of the mixture in the pipe.

11. The apparatus of claim 1 wherein said signal processor comprises logic which calculates a fluid composition of the mixture using the following relation:

$$a_{mix} = \sqrt{\frac{1 + \frac{\rho_1}{\rho_2}\frac{h_2}{h_1}}{\frac{1}{a_1^2} + \frac{\rho_1}{\rho_2}\frac{h_2}{h_1}\frac{1}{a_2^2}}}$$

where $a_1, a_2$ are known speeds of sound, $\rho_1, \rho_2$ are known densities, and $h_1, h_2$ are volume fractions of the two respective fluids, and $a_{mix}$ is the speed of sound of the mixture.

12. The apparatus of claim 1 wherein said speed of sound is substantially determined by two fluids within the mixture.

13. The apparatus of claim 12 wherein said two fluids are: oil/water, oil/gas, or water/gas.

14. The apparatus of claim 1 wherein said pressure sensors are fiber optic pressure sensors.

15. The apparatus of claim 1 wherein at least one of said pressure sensors comprises a fiber optic Bragg grating-based pressure sensor.

16. The apparatus of claim 1 wherein each of said pressure sensors measures a circumference-averaged pressure at said axial location of said sensor.

17. The apparatus of claim 1 wherein at least one of said pressure sensors measures pressure at more than one point around a circumference of the pipe at said given axial location of said sensor.

18. The apparatus of claim 1 wherein at least one of said pressure sensors measures strain on the pipe.

19. A method for measuring at least one parameter of a mixture of at least one fluid in a pipe, said method comprising:
measuring circumference-averaged acoustic pressures within the pipe at least two predetermined axial measurement locations along the pipe; and
calculating a speed of sound of the mixture using said acoustic pressures measured at said axial measurement locations.

20. The method of claim 19 wherein said calculating step comprises calculating a speed at which sound propagates along said axial measurement locations.

21. The method of claim 19 wherein said calculating step comprises calculating a frequency based signals for said acoustic pressures.

22. The method of claim 21 wherein said calculating step comprises calculating a ratio of two of said frequency based signals.

23. The method of claim 19 wherein said measuring step comprises measuring acoustic pressure at least three axial measurement locations along the pipe.

24. The method of claim 19 wherein said measuring step comprises measuring acoustic pressures at three axial measurement locations along the pipe and wherein said calculating step comprises simultaneously solving the following equations for the speed of sound:

$$P(x_1,t) = (Ae^{-ik_r x_1} + Be^{+ik_l x_1})e^{i\omega t}$$

$$P(x_2,t) = (Ae^{-ik_r x_2} + Be^{+ik_l x_2})e^{i\omega t}$$

$$P(x_3,t) = (Ae^{-ik_r x_3} + Be^{+ik_l x_3})e^{i\omega t}$$

where A,B are amplitudes of the frequency based signals, x is the axial location of the pressure sensor along the pipe, t is time, $\omega$ is frequency and $k_r, k_l$ are wave numbers.

25. The method of claim 19 wherein said calculating step calculates said speed of sound of the mixture using the following relation:

$$\frac{e^{-ik_r x_1} + Re^{ik_l x_1}}{e^{-ik_r x_3} + Re^{ik_l x_3}} - \left[\frac{P_1(\omega)}{P_3(\omega)}\right] = 0 \quad \text{where}$$

$$R \equiv \frac{B}{A} = \frac{e^{-ik_r x_1} - \left[\frac{P_1(\omega)}{P_2(\omega)}\right]e^{-ik_r x_2}}{\left[\frac{P_1(\omega)}{P_2(\omega)}\right]e^{ik_l x_2} - e^{ik_l x_1}} \quad \text{where}$$

$$k_r \equiv \left(\frac{\omega}{a_{mix}}\right)\frac{1}{1 + M_x} \quad \text{and} \quad k_l \equiv \left(\frac{\omega}{a_{mix}}\right)\frac{1}{1 - M_x}$$

where $a_{mix}$ is the speed of sound of the mixture in the pipe, $\omega$ is frequency (in rad/sec), and $M_x$ is the axial Mach number of the flow of the mixture within the pipe, where:

$$M_x \equiv \frac{V_{mix}}{a_{mix}}$$

and where Vmix is the axial velocity of the mixture, and where $P_1(\omega), P_2(\omega), P_3(\omega)$ are said frequency based signals for each of said acoustic pressures.

26. The method of claim 19 wherein said measurement locations are equally axially spaced, a Mach number of the mixture is small, and said calculating step calculates the speed of sound of the mixture using the following relation:

$$a_{mix} = \frac{\omega}{\left[\frac{1}{\Delta x}\right]i\log\left[\frac{P_{12} + P_{13}P_{12} + (P_{12}^2 + 2P_{13}P_{12}^2 + P_{13}^2 P_{12}^2 - 4P_{13}^2)^{1/2}}{2P_{13}}\right]}$$

A where $P_{12} = P_1(\omega)/P_2(\omega), P_{13} = P_1(\omega)/P_3(\omega)$, i is the square root of $-1$, $\Delta x$ is the axial spacing between sensors, where $a_{mix}$ is the speed of sound of the mixture in the pipe, $\omega$ is frequency (in rad/sec), and where $P_1(\omega), P_2(\omega), P_3(\omega)$ are said frequency based signals for each of said acoustic pressures.

27. The method of claim 19 wherein said measurement locations are equally axially spaced, a Mach number of the mixture is small compared to one, and said calculating step calculates the speed of sound of the mixture using the following relation:

$$\frac{P_1(\omega) + P_3(\omega)}{P_2(\omega)} = 2\cos\left(\frac{\omega \Delta x}{a_{mix}}\right)$$

where $a_{mix}$ is the speed of sound of the mixture in the pipe, $\omega$ is frequency (in rad/sec), $\Delta x$ is the axial spacing between said measurement locations, and where $P_1(\omega), P_2(\omega), P_3(\omega)$ are said frequency based signals for each of said acoustic pressures.

28. The method of claim 19 further comprising calculating a fluid composition of the mixture in the pipe.

29. The apparatus of claim 19 further comprising calculating a fluid composition of the mixture using the following relation:

$$a_{mix} = \sqrt{\frac{1 + \frac{\rho_1}{\rho_2}\frac{h_2}{h_1}}{\frac{1}{a_1^2} + \frac{\rho_1}{\rho_2}\frac{h_2}{h_1}\frac{1}{a_2^2}}}$$

where $a_1, a_2$ are known speeds of sound, $\rho_1, \rho_2$ are known densities, and $h_1, h_2$ are volume fractions of the two respective fluids, $a_{mix}$ is the speed of sound of the mixture.

30. The method of claim 19 wherein the speed of sound is substantially determined by two fluids within the mixture.

31. The method of claim 30 wherein said two fluids are: oil/water, oil/gas, or water/gas.

32. The method of claim 19 wherein said measuring step is performed by fiber optic pressure sensors.

33. The method of claim 19 wherein said measuring step is performed by fiber optic Bragg grating-based pressure sensors.

34. The method of claim 19 wherein said measuring step measures a circumference-averaged pressure at said axial location of said sensor.

35. The method of claim 19 wherein said measuring step measures pressure at more than one point around a circumference of the pipe at said axial location of said sensor.

36. An apparatus for measuring at least one parameter of a mixture of at least one fluid in a pipe, comprising:

a spatial array of at least two pressure sensors, disposed at different axial locations along the pipe, and each measuring an acoustic pressure associated with a background acoustic noise within the pipe at a corresponding axial location, each of said sensors providing an acoustic pressure signal indicative of the background acoustic noise within the pipe at said axial location of a corresponding one of said sensors; and a signal processor, responsive to said pressure signals, which provides a signal indicative of a speed of sound of the mixture in the pipe.

37. The apparatus of claim 36 wherein said signal processor comprises logic which calculates a speed at which sound propagates along said spatial array.

38. The apparatus of claim 36 wherein said signal processor comprises logic which calculates a frequency based signal for each of said acoustic pressure signals.

39. The apparatus of claim 37 wherein said acoustic pressure signals each comprise a frequency based signal and wherein said signal processor comprises logic which calculates a ratio of two of said frequency based signals.

40. The apparatus of claim 36 wherein said background acoustic noise is produced by a non-explicit source.

41. The apparatus of claim 36 wherein the signal processor comprises logic which calculates a fluid composition of the mixture in the pipe.

42. The apparatus of claim 36 wherein said signal processor comprises logic which calculates a fluid composition of the mixture using the following relation:

$$a_{mix} = \sqrt{\frac{1 + \frac{\rho_1}{\rho_2}\frac{h_2}{h_1}}{\frac{1}{a_1^2} + \frac{\rho_1}{\rho_2}\frac{h_2}{h_1}\frac{1}{a_2^2}}}$$

where $a_1, a_2$ are known speeds of sound, $\rho_1, \rho_2$ are known densities, and $h_1, h_2$ are volume fractions of the two respective fluids, and $a_{mix}$ is the speed of sound of the mixture.

43. The apparatus of claim 36 wherein said speed of sound is substantially determined by two fluids within the mixture.

44. The apparatus of claim 43 wherein said two fluids are: oil/water, oil/gas, or water/gas.

45. The apparatus of claim 36 wherein said pressure sensors are fiber optic pressure sensors.

46. The apparatus of claim 36 wherein at least one of said pressure sensors comprises a fiber optic Bragg grating-based pressure sensor.

47. The apparatus of claim 36 wherein each of said pressure sensors measures a circumference-averaged pressure at said axial location of said sensor.

48. The apparatus of claim 36 wherein at least one of said pressure sensors measures pressure at more than one point around a circumference of the pipe at said given axial location of said sensor.

49. The apparatus of claim 36 wherein at least one of said pressure sensors measures strain on the pipe.

50. A method for measuring at least one parameter of a mixture of at least one fluid in a pipe, said method comprising:

measuring acoustic pressures associated with a background acoustic noise within the pipe at least two predetermined axial measurement locations along the pipe; and calculating a speed of sound of the mixture using said acoustic pressures measured at said axial measurement locations.

51. The method of claim 50 wherein said calculating step comprises calculating a speed at which sound propagates along said axial measurement locations.

52. The method of claim 50 wherein said calculating step comprises calculating frequency based signals for said acoustic pressures.

53. The method of claim 52 wherein said calculating step comprises calculating a ratio of two of said frequency based signals.

54. The method of claim 50 further comprising calculating a fluid composition of the mixture in the pipe.

55. The apparatus of claim 50 further comprising calculating a fluid composition of the mixture using the following relation:

$$a_{mix} = \sqrt{\frac{1 + \frac{\rho_1}{\rho_2}\frac{h_2}{h_1}}{\frac{1}{a_1^2} + \frac{\rho_1}{\rho_2}\frac{h_2}{h_1}\frac{1}{a_2^2}}}$$

where $a_1, a_2$ are known speeds of sound, $\rho_1, \rho_2$ are known densities, and $h_1, h_2$ are volume fractions of the two respective fluids, $a_{mix}$ is the speed of sound of the mixture.

56. The method of claim 50 wherein the speed of sound is substantially determined by two fluids within the mixture.

57. The method of claim 56 wherein said two fluids are: oil/water, oil/gas, or water/gas.

58. The method of claim 50 wherein said measuring step is performed by fiber optic pressure sensors.

59. The method of claim 50 wherein said measuring step is performed by fiber optic Bragg grating-based pressure sensors.

60. The method of claim 50 wherein said measuring step measures a circumference-averaged pressure at said axial location of said sensor.

61. The method of claim 50 wherein said measuring step measures pressure at more than one point around a circumference of the pipe at said axial location of said sensor.

62. An apparatus for measuring at least one parameter of a mixture of at least one fluid in a pipe, comprising:

a spatial array of at least three pressure sensors, disposed at different axial locations along the pipe, and each measuring an acoustic pressure within the pipe at a corresponding axial location, each of said sensors providing an acoustic pressure signal indicative of the acoustic pressure within the pipe at said axial location of a corresponding one of said sensors; and a signal processor, responsive to said pressure signals, which provides a frequency based signal indicative of a speed of sound of the mixture in the pipe wherein said signal processor comprises logic which simultaneously solves the following equations for said speed of sound:

$$P(x_1,t)=(Ae^{-ik_r x_1}+Be^{+ik_l x_1})e^{i\omega t}$$

$$P(x_2,t)=(Ae^{-ik_r x_2}+Be^{+ik_l x_2})e^{i\omega t}$$

$$P(x_3,t)=(Ae^{-ik_r x_3}+Be^{+ik_l x_3})e^{i\omega t}$$

where A,B are amplitudes of the frequency based signals, x is the axial location of the pressure sensor along the pipe, t is time, $\omega$ is frequency and $k_r, k_l$ are wave numbers.

63. The apparatus of claim 62 wherein said signal processor calculates said speed of sound of said mixture using the following relation:

$$\frac{e^{-ik_r x_1}+Re^{ik_l x_1}}{e^{-ik_r x_3}+Re^{ik_l x_3}} - \left[\frac{P_1(\omega)}{P_3(\omega)}\right] = 0$$

$$\text{where } R \equiv \frac{B}{A} = \frac{e^{-ik_r x_1} - \left[\frac{P_1(\omega)}{P_2(\omega)}\right]e^{-ik_r x_2}}{\left[\frac{P_1(\omega)}{P_2(\omega)}\right]e^{ik_l x_2} - e^{ik_l x_1}}$$

$$\text{where } k_r \equiv \left(\frac{\omega}{a_{mix}}\right)\frac{1}{1+M_x} \quad \text{and} \quad k_l \equiv \left(\frac{\omega}{a_{mix}}\right)\frac{1}{1-M_x}$$

where $a_{mix}$ is the speed of sound of the mixture in the pipe, $\omega$ is frequency (in rad/sec), and $M_x$ is the axial Mach number of the flow of the mixture within the pipe, where:

$$M_x \equiv \frac{V_{mix}}{a_{mix}}$$

and where Vmix is the axial velocity of the mixture, and where $P_1(\omega), P_2(\omega), P_3(\omega)$ are said frequency based signals for each of said acoustic pressure signals.

64. The apparatus of claim 62 wherein said sensors are equally spaced, a Mach number of the mixture is small compared to one, and said signal processor calculates the speed of sound of the mixture using the following relation:

$$a_{mix} = \frac{\omega}{\left[\frac{1}{\Delta x}\right] i \log\left[\frac{P_{12}+P_{13}P_{12}+(P_{12}^2+2P_{13}P_{12}^2+P_{13}^2 P_{12}^2-4P_{13}^2)^{1/2}}{2P_{13}}\right]}$$

where $P_{12}=P_1(\omega)/P_2(\omega), P_{13}=P_1(\omega)/P_3(\omega)$, i is the square root of −1, $\Delta x$ is the axial spacing between sensors, where $a_{mix}$ is the speed of sound of the mixture in the pipe, $\omega$ is frequency (in rad/sec), and where $P_1(\omega), P_2(\omega), P_3(\omega)$ are said frequency based signals for each of said acoustic pressure signals.

65. The apparatus of claim 62 wherein said sensors are equally axially spaced, a Mach number of the mixture is small compared to one, and said signal processor calculates the speed of sound of the mixture using the following relation:

$$\frac{P_1(\omega)+P_3(\omega)}{P_2(\omega)} = 2\cos\left(\frac{\omega \Delta x}{a_{mix}}\right)$$

where $a_{mix}$ is the speed of sound of the mixture in the pipe, $\omega$ is frequency (in rad/sec), $\Delta x$ is the axial spacing between said sensors, and where $P_1(\omega), P_2(\omega), P_3(\omega)$ are said frequency based signals for each of said acoustic pressures signals.

66. The apparatus of claim 62 wherein the signal processor comprises logic which calculates a fluid composition of the mixture in the pipe.

67. The apparatus of claim 62 wherein said signal processor comprises logic which calculates a fluid composition of the mixture using the following relation:

$$a_{mix} = \sqrt{\frac{1+\frac{\rho_1}{\rho_2}\frac{h_2}{h_1}}{\frac{1}{a_1^2}+\frac{\rho_1}{\rho_2}\frac{h_2}{h_1}\frac{1}{a_2^2}}}$$

where $a_1, a_2$ are known speeds of sound, $\rho_1, \rho_2$ are known densities, and $h_1, h_2$ are volume fractions of the two respective fluids, and $a_{mix}$ is the speed of sound of the mixture.

68. The apparatus of claim 62 wherein said speed of sound is substantially determined by two fluids within the mixture.

69. The apparatus of claim 68 wherein said two fluids are: oil/water, oil/gas, or water/gas.

70. The apparatus of claim 62 wherein said pressure sensors are fiber optic pressure sensors.

71. The apparatus of claim 62 wherein at least one of said pressure sensors comprises a fiber optic Bragg grating-based pressure sensor.

72. The apparatus of claim 62 wherein at least one of said pressure sensors measures pressure at more than one point around a circumference of the pipe at said given axial location of said sensor.

73. The apparatus of claim 62 wherein at least one of said pressure sensors measures strain on the pipe.

74. A method for measuring at least one parameter of a mixture of at least one fluid in a pipe, said method comprising:

measuring circumference-averaged acoustic pressures within the pipe at least three predetermined axial measurement locations along the pipe; and calculating a speed of sound of the mixture using said acoustic pressures measured at said axial measurement locations by simultaneously solving the following equations for the speed of sound:

$$P(x_1,t)=(Ae^{-ik_rx_1}+Be^{+ik_lx_1})e^{i\omega t}$$

$$P(x_2,t)=(Ae^{-ik_rx_2}+Be^{+ik_lx_2})e^{i\omega t}$$

$$P(x_3,t)=(Ae^{-ik_rx_3}+Be^{+ik_lx_3})e^{i\omega t}$$

where A,B are amplitudes of the frequency based signals, x is the axial location of the pressure sensor along the pipe, t is time, $\omega$ is frequency and $k_r, k_l$ are wave numbers.

75. The method of claim 74 wherein said calculating step comprises calculating frequency based signals for said acoustic pressures.

76. The method of claim 75 wherein said calculating step comprises calculating a ratio of two of said frequency based signals.

77. The method of claim 74 wherein said calculating step calculates said speed of sound of the mixture using the following relation:

$$\frac{e^{-ik_rx_1}+Re^{ik_lx_1}}{e^{-ik_rx_3}+Re^{ik_lx_3}} - \left[\frac{P_1(\omega)}{P_3(\omega)}\right] = 0$$

$$\text{where } R \equiv \frac{B}{A} = \frac{e^{-ik_rx_1} - \left[\frac{P_1(\omega)}{P_2(\omega)}\right]e^{-ik_rx_2}}{\left[\frac{P_1(\omega)}{P_2(\omega)}\right]e^{ik_lx_2} - e^{ik_lx_1}}$$

$$\text{where } k_r \equiv \left(\frac{\omega}{a_{mix}}\right)\frac{1}{1+M_x} \text{ and } k_l \equiv \left(\frac{\omega}{a_{mix}}\right)\frac{1}{1-M_x}$$

where $a_{mix}$ is the speed of sound of the mixture in the pipe, $\omega$ is frequency (in rad/sec), and $M_x$ is the axial Mach number of the flow of the mixture within the pipe, where:

$$M_x \equiv \frac{V_{mix}}{a_{mix}}$$

and where Vmix is the axial velocity of the mixture, and where $P_1(\omega), P_2(\omega), P_3(\omega)$ are said frequency based signals for each of said acoustic pressures.

78. The method of claim 74 wherein said measurement locations are equally axially spaced, a Mach number of the mixture is small, and said calculating step calculates the speed of sound of the mixture using the following relation:

$$a_{mix} = \frac{\omega}{\left[\frac{1}{\Delta x}\right]i\log\left[\frac{P_{12}+P_{13}P_{12}+(P_{12}^2+2P_{13}P_{12}^2+P_{13}^2P_{12}^2-4P_{13}^2)^{1/2}}{2P_{13}}\right]}$$

where $P_{12}=P_1(\omega)/P_2(\omega), P_{13}=P_1(\omega)/P_3(\omega)$, i is the square root of −1, $\Delta x$ is the axial spacing between sensors, where $a_{mix}$ is the speed of sound of the mixture in the pipe, $\omega$ is frequency (in rad/sec), and where $P_1(\omega), P_2(\omega), P_3(\omega)$ are said frequency based signals for each of said acoustic pressures.

79. The method of claim 74 wherein said measurement locations are equally axially spaced, a Mach number of the mixture is small compared to one, and said calculating step calculates the speed of sound of the mixture using the following relation:

$$\frac{P_1(\omega)+P_3(\omega)}{P_2(\omega)} = 2\cos\left(\frac{\omega\Delta x}{a_{mix}}\right)$$

where $a_{mix}$ is the speed of sound of the mixture in the pipe, $\omega$ is frequency (in rad/sec), $\Delta x$ is the axial spacing between said measurement locations, and where $P_1(\omega), P_2(\omega), P_3(\omega)$ are said frequency based signals for each of said acoustic pressures.

80. The method of claim 74 further comprising calculating a fluid composition of the mixture in the pipe.

81. The apparatus of claim 74 further comprising calculating a fluid composition of the mixture using the following relation:

$$a_{mix} = \sqrt{\frac{1+\frac{\rho_1}{\rho_2}\frac{h_2}{h_1}}{\frac{1}{a_1^2}+\frac{\rho_1}{\rho_2}\frac{h_2}{h_1}\frac{1}{a_2^2}}}$$

where $a_1, a_2$ are known speeds of sound, $\rho_1, \rho_2$ are known densities, and $h_1, h_2$ are volume fractions of the two respective fluids, $a_{mix}$ is the speed of sound of the mixture.

82. The method of claim 74 wherein the speed of sound is substantially determined by two fluids within the mixture.

83. The method of claim 81 wherein said two fluids are: oil/water, oil/gas, or water/gas.

84. The method of claim 74 wherein said measuring step is performed by fiber optic pressure sensors.

85. The method of claim 74 wherein said measuring step is performed by fiber optic Bragg grating-based pressure sensors.

86. The method of claim 74 wherein said measuring step measures pressure at more than one point around a circumference of the pipe at said axial location of said sensor.

* * * * *

UNITED STATES PATENT AND TRADEMARK OFFICE
CERTIFICATE OF CORRECTION

PATENT NO. : 6,354,147 B1
DATED : March 12, 2002
INVENTOR(S) : Daniel L. Gysling, Alan D. Kersey and James D. Paduano It is certified that error appears in the above-identified patent and that said Letters Patent is hereby corrected as shown below:

Column 24,
Line 20, delete "$P(x_1,t) = \left(Ae^{-ik_r x_1} + Be^{+ik_1 x_1}\right)e^{i\omega t}$" and insert -- $P(x_1,t) = \left(Ae^{-ik_r x_1} + Be^{+ik_i x_1}\right)e^{i\omega t}$ --
Line 21, delete "$P(x_2,t) = \left(Ae^{-ik_r x_2} + Be^{+ik_1 x_2}\right)e^{i\omega t}$" and insert -- $P(x_2,t) = \left(Ae^{-ik_r x_2} + Be^{+ik_i x_2}\right)e^{i\omega t}$ --
Line 22, delete "$P(x_3,t) = \left(Ae^{-ik_r x_3} + Be^{+ik_1 x_3}\right)e^{i\omega y}$" and insert -- $P(x_3,t) = \left(Ae^{-ik_r x_3} + Be^{+ik_i x_3}\right)e^{i\omega t}$ --

Line 48, delete "Vmix" and insert -- $V_{mix}$ --
Line 65, delete "P$_2$()," and insert -- P$_2(\omega)$, --

Column 25,
Line 13, delete "pressures" and insert -- pressure --
Line 51, delete "at least" and insert -- at at least --
Line 60, delete "signals" and insert -- signal --
Line 66, delete "at least" and insert -- at at least --

Column 26,
Line 7, delete "$P(x_1,t) = \left(Ae^{-ik_r x_1} + Be^{+ik_1 x_1}\right)e^{i\omega t}$" and insert -- $P(x_1,t) = \left(Ae^{-ik_r x_1} + Be^{+ik_i x_1}\right)e^{i\omega t}$ --
Line 9, delete "$P(x_2,t) = \left(Ae^{-ik_r x_2} + Be^{+ik_1 x_2}\right)e^{i\omega t}$" and insert -- $P(x_2,t) = \left(Ae^{-ik_r x_2} + Be^{+ik_i x_2}\right)e^{i\omega t}$ --
Line 10, delete "$P(x_3,t) = \left(Ae^{-ik_r x_3} + Be^{+ik_1 x_3}\right)e^{i\omega t}$" and insert -- $P(x_3,t) = \left(Ae^{-ik_r x_3} + Be^{+ik_i x_3}\right)e^{i\omega t}$ --

Line 37, delete "Vmix" and insert -- $V_{mix}$ --
Line 50, delete "A"

Column 28,
Line 32, delete "at least" and insert -- at at least --

Column 29,
Line 28, delete "$P(x_1,t) = \left(Ae^{-ik_r x_1} + Be^{+ik_1 x_1}\right)e^{i\omega t}$" and insert -- $P(x_1,t) = \left(Ae^{-ik_r x_1} + Be^{+ik_i x_1}\right)e^{i\omega t}$ --
Line 30, delete "$P(x_2,t) = \left(Ae^{-ik_r x_2} + Be^{+ik_1 x_2}\right)e^{i\omega t}$" and insert -- $P(x_2,t) = \left(Ae^{-ik_r x_2} + Be^{+ik_i x_2}\right)e^{i\omega t}$ --
Line 32, delete "$P(x_3,t) = \left(Ae^{-ik_r x_3} + Be^{+ik_1 x_3}\right)e^{i\omega t}$" and insert -- $P(x_3,t) = \left(Ae^{-ik_r x_3} + Be^{+ik_i x_3}\right)e^{i\omega t}$ --

Line 45, delete "where $R \equiv \dfrac{B}{A} = \dfrac{e^{-ik_r x_1} - \left[\dfrac{P_1(\omega)}{P_2(\omega)}\right]e^{-ik_r x_2}}{\left[\dfrac{P_1(\omega)}{P_2(\omega)}\right]e^{ik_r x_2} - e^{ik_r x_1}}$," and insert -- where $R \equiv \dfrac{B}{A} = \dfrac{e^{-ik_i x_1} - \left[\dfrac{P_1(\omega)}{P_2(\omega)}\right]e^{-ik_i x_2}}{\left[\dfrac{P_1(\omega)}{P_2(\omega)}\right]e^{ik_i x_2} - e^{ik_i x_1}}$ --

Line 60, delete "Vmix" and insert -- $V_{mix}$ --

UNITED STATES PATENT AND TRADEMARK OFFICE
CERTIFICATE OF CORRECTION

PATENT NO.   : 6,354,147 B1
DATED        : March 12, 2002
INVENTOR(S)  : Daniel L. Gysling, Alan D. Kersey and James D. Paduano It is certified that error appears in the above-identified patent and that said Letters Patent is hereby corrected as shown below:

Column 30,
Line 62, delete "at least" and insert -- at at least --

Column 31,
Line 1, delete " $P(x_1,t) = \left(Ae^{-ik_r x_1} + Be^{+ik_1 x_1}\right)e^{i\omega t}$ " and insert -- $P(x_1,t) = \left(Ae^{-ik_r x_1} + Be^{+ik_1 x_1}\right)e^{i\omega t}$ --
Line 2, delete " $P(x_2,t) = \left(Ae^{-ik_r x_2} + Be^{+ik_1 x_2}\right)e^{i\omega t}$ " and insert -- $P(x_2,t) = \left(Ae^{-ik_r x_2} + Be^{+ik_1 x_2}\right)e^{i\omega t}$ --
Line 3, delete " $P(x_3,t) = \left(Ae^{-ik_r x_3} + Be^{+ik_1 x_3}\right)e^{i\omega t}$ " and insert -- $P(x_3,t) = \left(Ae^{-ik_r x_3} + Be^{+ik_1 x_3}\right)e^{i\omega t}$ --

Line 36, delete "Vmix" and insert -- $V_{mix}$ --

Signed and Sealed this

Sixth Day of August, 2002

Attest:

JAMES E. ROGAN
Attesting Officer        Director of the United States Patent and Trademark Office